US009668501B2

(12) United States Patent
Steinberg et al.

(10) Patent No.: US 9,668,501 B2
(45) Date of Patent: Jun. 6, 2017

(54) USE OF BACTERIAL AMYLASES IN FEED FOR BOVINE ANIMALS

(75) Inventors: Wolfgang Steinberg, Efringen-Kirchen (DE); Immig Irmgard, Habsburg (CH); Vibe Glitsoe, Virum (DK); Morten Fischer, Copenhagen V (DK)

(73) Assignees: DSM IP Assets B.V., Heerlen (NL); Novozymes A/S, Bagsvaerd (DK)

( * ) Notice: Subject to any disclaimer, the term of this patent is extended or adjusted under 35 U.S.C. 154(b) by 667 days.

(21) Appl. No.: 12/307,997

(22) PCT Filed: Jul. 12, 2007

(86) PCT No.: PCT/EP2007/057189
§ 371 (c)(1),
(2), (4) Date: Feb. 25, 2009

(87) PCT Pub. No.: WO2008/006881
PCT Pub. Date: Jan. 17, 2008

(65) Prior Publication Data
US 2009/0324571 A1    Dec. 31, 2009

Related U.S. Application Data

(60) Provisional application No. 60/831,179, filed on Jul. 14, 2006.

(30) Foreign Application Priority Data

Jul. 13, 2006    (DK) ................................ 2006 00974

(51) Int. Cl.
| | | |
|---|---|---|
| *A61K 38/54* | (2006.01) |
| *A23K 50/10* | (2016.01) |
| *A23K 10/37* | (2016.01) |
| *A23K 10/14* | (2016.01) |

(52) U.S. Cl.
CPC .............. *A23K 50/10* (2016.05); *A23K 10/14* (2016.05); *A23K 10/37* (2016.05); *Y02P 60/877* (2015.11)

(58) Field of Classification Search
None
See application file for complete search history.

(56) References Cited

U.S. PATENT DOCUMENTS

| | | | |
|---|---|---|---|
| 3,250,622 A | 5/1966 | Brooks et al. | |
| 6,177,012 B1 | 1/2001 | Lawler et al. | |
| 2002/0122846 A1 | 9/2002 | Drouillard et al. | |
| 2002/0187528 A1 | 12/2002 | Veit et al. | |
| 2004/0043058 A1* | 3/2004 | Cobb et al. | 424/442 |
| 2004/0235125 A1 | 11/2004 | Kottwitz et al. | |
| 2006/0014265 A1* | 1/2006 | Ferrari et al. | 435/204 |
| 2009/0047266 A1* | 2/2009 | Svendsen et al. | 424/94.2 |

FOREIGN PATENT DOCUMENTS

| | | | |
|---|---|---|---|
| EP | 0594235 A2 | 9/1994 | |
| EP | 1 415 539 | 6/2004 | |
| GB | 2 134 767 | 8/1984 | |
| NZ | 524303 | 6/2004 | |
| WO | WO 92/19744 | 11/1992 | |
| WO | WO 96/08261 | 3/1996 | |
| WO | WO 00/12746 | 3/2000 | |
| WO | WO 01/41795 | * 6/2001 | ............. A61K 38/48 |
| WO | WO 03/049550 | 6/2003 | |
| WO | WO 03/068256 | 8/2003 | |
| WO | WO 2004/026048 | 4/2004 | |
| WO | 2004/078960 A1 | 9/2004 | |
| WO | WO 2005/053434 | 6/2005 | |
| WO | WO 2006/002495 | 1/2006 | |
| WO | WO 2006/128469 | 12/2006 | |

OTHER PUBLICATIONS

Perry et al., Department of Animal Sciences Journal Paper Xo. 2664, 1966, pp. 760-764.*
van Wallenghem et al., Florida Agricultural Experiment Stations, Journal Series No. 1864, 1964, pp. 960-962.*
DeFrain et al., J. Dairy Sci., 88:4405-4413 (2005)).*
Day et al., Database WPI, Accession No. 2004-716650 (2004).
Pantschev et al., Database FSTA (IFIS), Accession No. 82-3-03-a0223 (1981).
Inoue Naoto et al., Database Biosis, Accession No. PREV199395023440 (1992).
Tolokonnikov et al., Database FSTA, Accession No. 75-1-09-g0533 (1975).
Antunovic et al., Database Accession No. 1998-10s11703 FSTA, (1998).
Guttierrez et al., Journal of Applied Animal Research, vol. 27, No. 1, pp. 7-10 (2005).
Rojo et al., Animal Feed Science and Technology. vol. 123-124, pp. 655-665 (2005).
Tricarico et al., Animal Science, vol. 81, pp. 365-374 (2005).
Mora-Jaimes et al., Agrociencia, vol. 36, pp. 31-39 (2002).
Tolokonnikov et al., Zhivotnovodstvo, vol. 4, pp. 78-79 (1975).
Inoue Naoto et al., Journal of Japanese Society of Grassland Science, vol. 37, No. 4, pp. 397-404 (1992).
Pantschev et al., Lebensmittelindustrie, vol. 28, No. 2, pp. 71-74 (1981).
Allerdings et al., Phytochemistry, vol. 67, pp. 1276-1286 (2006).
Van der Veen et al., Journal of Food Engineering, vol. 75, pp. 178-186 (2006).
Atichokudomchai et al., Carbohydrate Polymers, vol. 64, pp. 582-588 (2006).

(Continued)

*Primary Examiner* — Irene Marx
(74) *Attorney, Agent, or Firm* — Elias Lambiris

(57) ABSTRACT

The invention relates to the use of at least one bacterial amylase in feed for ruminant animals of the subfamily Bovinae in particular for improving milk yield, apparent digestibility of the diet fed, feedstuff dry matter disappearance, weight gain, and/or Feed Conversion Ratio (FCR). Examples of bovine animals are dairy cows and beef cattle. The invention also relates to the use of such amylases in feed and feed additives such as premix, concentrates and total mixed ration (TMR). The amylase may be used in combination with cellulase for improving milk yield and/or back fat thickness. Preferred amylases are derived from *Bacillus halmapalus*, *licheniformis*, and *stearothermophilus* and are preferably homologous to *Bacillus stearothermophilus* amylase.

10 Claims, 2 Drawing Sheets

(56) References Cited

OTHER PUBLICATIONS

Figure 1:
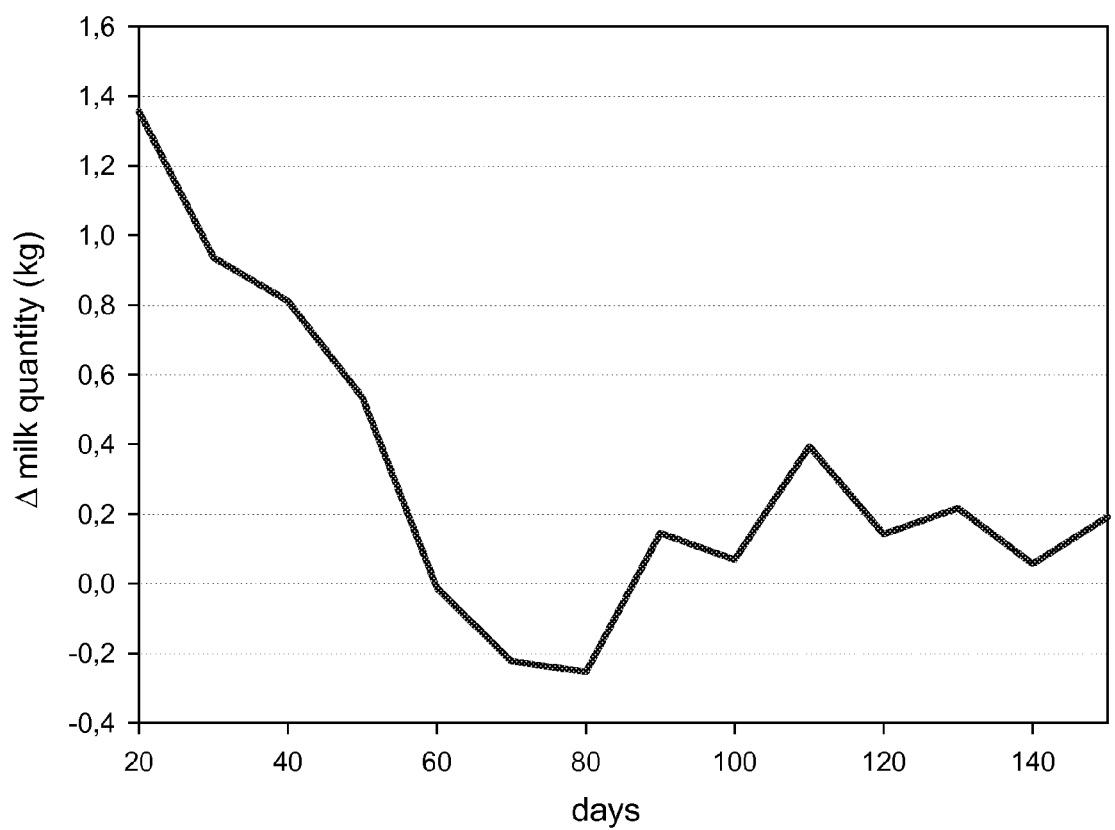

Yoon et al., Lebensmittel Wissenschaft und Technologie, vol. 39, pp. 387-391 (2006).
Klenz et al., Database FSTA, Accession No. 84-1-04-L0198 (1984).
Gray et al., Journal of Bacteriology, vol. 166, No. 2, pp. 635-643 (1986).

* cited by examiner

USE OF BACTERIAL AMYLASES IN FEED FOR BOVINE ANIMALS

CROSS-REFERENCE TO RELATED APPLICATIONS

This application is a 35 U.S.C. 371 national application of PCT/EP2007/057189 filed Jul. 12, 2007, which claims priority or the benefit under 35 U.S.C. 119 of Danish application no. PA 2006 00974 filed Jul. 13, 2006 and U.S. provisional application No. 60/831,179 filed Jul. 14, 2006, the contents of which are fully incorporated herein by reference.

REFERENCE TO SEQUENCE LISTING

This application contains a Sequence Listing in computer readable form. The computer readable form is incorporated herein by reference.

BACKGROUND OF THE INVENTION

Field of the Invention

High-yielding cows in modern farming systems live under conditions that are characterised by a very high milk production (dairy cows) or growth rate (beef cattle), which is followed by an equally high energy requirement. The utilisation of the feed decreases markedly when intake is increased beyond maintenance levels. In part to account for this, more and more easily degradable feed is included into the ruminant feed e.g. starch-containing raw materials such a cereal-based concentrates and whole cereal silages. The starchy material is frequently recovered in the faeces implying that the utilisation of such feed ingredients could be enhanced further.

The present invention relates to the use of a bacterial amylase in feed for bovine animals such as dairy cows and beef cattle, in particular for improving milk yield, weight gain, apparent digestibility, disappearance of feedstuff dry matter using the nylon bag method, and/or feed conversion. The invention also relates to compositions such as feed and feed additives comprising the bacterial amylase, as well as methods of preparing such compositions.

Description of the Related Art

WO 03/068256 A1 describes an amylase feed supplement for improved ruminant nutrition. The amylase used is a fungal amylase produced by *Aspergillus oryzae*. Tricarico et al, in Animal Science 2005, 81: 365-374, describe the effects of *Aspergillus oryzae* extract containing alpha-amylase activity on ruminal fermentation and milk production in lactating Holstein cows.

U.S. Pat. No. 3,250,622 discloses the use of a specific additive containing proteolytic and amylolytic enzymes as well as gumase, intimately associated with a ground malt carrier, for stimulating milk production in dairy cows. The enzyme source is not specified.

Mora-Jaimes et al (Agrociencia 36(1) (2002), 31-39) studied the performance and ruminal fermentation in lambs fed sorghum grain treated with amylases.

Rojo et al (Animal Feed Science and Technology, 123-124 (2005), 655-665) studied the effects of exogenous amylases from *Bacillus licheniformis* and *Aspergillus niger* on ruminal starch digestion and lamb performance.

WO 01/41795 A1 relates to the use of a combination of a protease and an inner salt of a quaternary amine carboxylic acid in the treatment and/or prophylaxis of coccidiosis and bacterial infections. An improved weight gain of animals in general is also claimed. A xylanase and/or an amylase may be included. Alpha-amylase from *Bacillus subtilis* is mentioned. Ruminants are also mentioned, however all examples relate to broiler chicks.

It is an object of the present invention to provide alternative, preferably improved, amylases which may alleviate the problems described above by improving feed utilization, milk yield, and/or weight gain. The amylases of the invention furthermore, or in the alternative, may have improved properties such as dose-response profile, pH-profile, pelleting-stability, temperature-stability, bile-salt stability, protease-stability, and/or specific activity. The amylases of the invention may furthermore, or in the alternative, be capable of degrading starch in the rumen, in the large intestines, and/or in the small intestines.

SUMMARY OF THE INVENTION

The present invention relates to the use of at least one bacterial amylase in feed for animals of the subfamily Bovinae, in particular for improving milk yield, weight gain, feed digestibility, and/or Feed Conversion Ratio (FCR).

The invention also relates to the use of at least one bacterial amylase in the preparation of a composition for use in a feed for animals of the subfamily Bovinae.

The invention furthermore relates to feed additive compositions comprising at least one bacterial amylase, together with at least one additional ingredient selected from vitamins and/or minerals.

Finally, the invention relates to a composition comprising at least one bacterial amylase together with at least one additional ingredient selected from hay, forage, roughage, and/or feed concentrate. Examples of such compositions are feed concentrates and Total Mixed Ration (TMR).

DETAILED DESCRIPTION OF THE INVENTION

In the present context, an amylase is an enzyme that catalyzes the endo-hydrolysis of starch and other linear and branched oligo- and polysaccharides. In a particular embodiment, the amylase for use according to the invention has alpha-amylase activity, viz. catalyzes the endohydrolysis of 1,4-alpha-glucosidic linkages in oligosaccharides and polysaccharides. Alpha-amylases act, e.g., on starch, glycogen and related polysaccharides and oligosaccharides in a random manner, liberating reducing groups in the alpha-configuration.

In a preferred embodiment the amylase of the invention is an alpha-amylase (systematical name: 1,4-alpha-D-glucan glucanohydrolase). In further embodiments, the amylase of the invention belongs to the EC 3.2.1.-group of amylases, such as EC 3.2.1.1 (alpha-amylase), EC 3.2.1.2 (beta-amylase), EC 3.2.1.3 (glucan 1,4-alpha-glucosidase, amyloglucosidase, or glucoamylase), EC 3.2.1.20 (alpha-glucosidase), EC 3.2.1.60 (glucan 1,4-alpha-maltotetraohydrolase), EC 3.2.1.68 (isoamylase), EC 3.2.1.98 (glucan 1,4-alpha-maltohexosidase), or EC 3.2.1.133 (glucan 1,4-alpha-maltohydrolase).

In a preferred embodiment, the amylase for use according to the invention can be, or is, classified as belonging to the EC 3.2.1.1 group. The EC numbers refer to Enzyme Nomenclature 1992 from NC-IUBMB, Academic Press, San Diego, Calif., including supplements 1-5 published in Eur. J. Biochem. 1994, 223, 1-5; Eur. J. Biochem. 1995, 232, 1-6; Eur. J. Biochem. 1996, 237, 1-5; Eur. J. Biochem. 1997, 250, 1-6; and Eur. J. Biochem. 1999, 264, 610-650; respectively. The nomenclature is regularly supplemented and updated; see e.g. the World Wide Web at http://www.chem.qmw.ac.uk/iubmb/enzyme/index.html.

Amylase activity may be determined by any suitable assay. Generally, assay-pH and assay-temperature may be adapted to the enzyme in question. Examples of assay-pH-values are pH 2, 3, 4, 5, 6, 7, 8, 9, 10, 11, or 12. Examples of assay-temperatures are 30, 35, 37, 40, 45, 50, 55, 60, 65, 70, 80, 90, or 95° C. Preferred pH values and temperatures are in the physiological range, such as pH values of 3, 4, 5, 6, 7, or 8, and temperatures of 30, 35, 37, or 40° C. A preferred assay is the KNU(S) assay of Example 5 herein. Another preferred assay is the reducing sugar assay of Example 6 herein. Alternatively, the following amylase assay can be used: Substrate: Phadebas tablets (Pharmacia Diagnostics; cross-linked, insoluble, blue-coloured starch polymer, which is mixed with bovine serum albumin and a buffer substance, and manufactured into tablets). Assay Temperature: 37° C. Assay pH: 4.3 (or 7.0, if desired). Reaction time: 20 min. After suspension in water the starch is hydrolyzed by the alpha-amylase, giving soluble blue fragments. The absorbance of the resulting blue solution, measured at 620 nm, is a function of the alpha-amylase activity. One Fungal alpha-Amylase Unit (1 FAU) is the amount of enzyme which breaks down 5.26 g starch per hour at the standard assay conditions. A preferred starch is Merck, Amylum solubile Erg. B. 6, Batch 9947275. A more detailed assay description, APTSMYQI-3207, is available on request from Novozymes A/S, Krogshoejvej 36, DK-2880 Bagsvaerd, Denmark.

In a particular embodiment, the amylase, in the form in which it is added to the feed, or when being included in a feed additive, is well-defined. Well-defined means, that the amylase preparation is at least 50% pure on a protein-basis. In other particular embodiments the amylase preparation is at least 60, 70, 80, 85, 88, 90, 92, 94, or at least 95% pure. Purity may be determined by any method known in the art, e.g. by SDS-PAGE, or by Size-exclusion chromatography (see Example 12 of WO 01/58275).

A well-defined amylase preparation is advantageous. For instance, it is much easier to dose correctly to the feed an amylase that is essentially free from interfering or contaminating other enzymes. The term dose correctly refers in particular to the objective of obtaining consistent and constant results, and the capability of optimising dosage based upon the desired effect.

Amylase preparations with purities of this order of magnitude are in particular obtainable using recombinant methods of production, whereas they are not so easily obtained and also subject to a much higher batch-to-batch variation when produced by traditional fermentation methods.

Isolation, purification, and concentration of the amylase of the invention may be carried out by conventional means. For example, it may be recovered from a fermentation broth by conventional procedures including, but not limited to, centrifugation, filtration, extraction, spray-drying, evaporation, or precipitation, and further purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulphate precipitation), SDS-PAGE, or extraction (see, e.g., Protein Purification, J.-C. Janson and Lars Ryden, editors, VCH Publishers, New York, 1989). The purified amylase may be formulated as is known in the art as a liquid or solid product suitable for use in animal feed and/or animal feed additives.

The bacterial amylase for use according to the invention is included in bovine diets or bovine feed additives in an effective amount. It is presently contemplated that an effective amount is below 1000 mg enzyme protein per kg diet dry matter (ppm), preferably below 800, 600, 500, 400, or below 300 ppm. In a preferred embodiment, the dosage of the amylase is below 200 mg enzyme protein per kg diet dry matter, preferably below 150, 100, 90, 80, 70, 60, or below 50 ppm. In an even more preferred embodiment, the dosage of the amylase is below 40, 35, 30, 25, or below 20 ppm. In a most preferred embodiment, the dosage of the amylase is below 15, 12, 10, 9, 8, or below 7 mg enzyme protein per kg diet dry matter. On the other hand, an effective amount may be above 0.01 mg enzyme protein per kg diet dry matter, preferably above 0.05, 0.10, 0.15, 0.20, 0.25, 0.30, 0.35, 0.40, 0.45, 0.50, 0.75, 1, 2, 3, or above 4 mg enzyme protein per kg diet dry matter (ppm). Accordingly, non-limiting examples of preferred dose ranges are: 0.10-50 mg enzyme protein/kg, preferably 0.50-10, 1-9, 2-8, 3-8, or 4-7 mg enzyme protein/kg. Additional examples of preferred dosage ranges, all in ppm, are: 1-35, 1-30, 2-25, 3-20, and 4-15.

For determining mg amylase protein per kg feed, the amylase is purified from the feed composition, and the specific activity of the purified amylase is determined using the desired amylase assay. The amylase activity of the feed composition as such is also determined using the same assay, and on the basis of these two determinations, the dosage in mg amylase enzme protein per kg feed is calculated.

The same principles apply for determining mg amylase protein in feed additives. Of course, if a sample is available of the amylase used for preparing the feed additive or the feed, the specific activity is determined from this sample (no need to purify the amylase from the feed composition or the additive).

For a taxonomical classification and identification of bacteria reference is had to Bergey's Manual of Systematic Bacteriology (1986), vol 2, ISBN0-683-0783. In the alternative, the well-known 16SrRNA sequence analysis can be used (see e.g. Johansen et al, Int. J. Syst. Bacteriol, 1999, 49, 1231-1240, in particular the Methods section on p. 1233, $2^{nd}$ column); or taxonomy experts can be consulted, e.g. from DSMZ or other recognized depositary institutes. As employed herein the term bacterial designates amylases that are derived from bacteria. The term "derived from" includes enzymes obtainable, or obtained, from wild type bacterial strains, as well as variants thereof. The variants may have at least one substitution, insertion, and/or deletion of at least one amino acid residue. The term variant also includes shufflants, hybrids, chimeric enzymes and consensus enzymes. The variants may have been produced by any method known in the art, such as site-directed mutagenesis, random mutagenesis, consensus derivation processes (EP 897985), and gene shuffling (WO 95/22625, WO 96/00343), etc. For the present purposes an amylase variant qualifies as bacterial when at least one bacterial amylase has been used for its design, derivation or preparation. The term bacterial does not refer to a potential recombinant production host but only to the origin of the amylase encoding gene that is hosted by it.

The amylase for use according to the invention is preferably derived from a strain of *Bacillus*, such as strains of *Bacillus amyloliquefaciens, Bacillus circulans, Bacillus halmapalus, Bacillus licheniformis, Bacillus megaterium, Bacillus* sp., *Bacillus stearothermophilus*, and *Bacillus subtilis*; preferably from strains of *Bacillus amyloliquefaciens, Bacillus halmapalus, Bacillus licheniformis, Bacillus* sp., *Bacillus subtilis*, and *Bacillus stearothermophilus*; more preferably from strains of *Bacillus amyloliquefaciens*, *Bacillus halmapalus*, *Bacillus licheniformis*, *Bacillus* sp., and *Bacillus stearothermophilus*; even more preferably from *Bacillus amyloliquefaciens*, *Bacillus halmapalus*, *Bacillus* sp., and *Bacillus stearothermophilus*; most preferably from *Bacillus stearothermophilus*.

Non-limiting examples of amylases for use according to the invention are those derived from *Bacillus licheniformis*, such as Swissprot entry name AMY_BACLI, primary accession number P06278; *Bacillus amyloliquefaciens*, such as Swissprot entry name AMY_BACAM, primary accession number P00692; *Bacillus megaterium*, such as Swissprot entry name AMY_BACME, primary accession number P20845; *Bacillus circulans*, such as Swissprot entry name AMY_BACCI, primary accession number P08137; *Bacillus stearothermophilus*, such as Swissprot entry name AMY_BACST, primary accession number P06279. Another example is from *Bacillus subtilis*, such as Swissprot entry name AMY_BACSU, primary accession number P00691.

For purposes of the present invention, preferred amylases are the amylases contained in the following commercial products: BAN, Stainzyme, Termamyl SC, Natalase, and Duramyl (all from Novozymes).

Further particular examples of amylases for use accoding to the invention are the amylases contained in the commercial Validase BAA and Validase HT products (from Valley Research).

Still further particular examples of amylases for use according to the invention are the amylases contained in the following commercial products: Clarase, DexLo, GC 262 SP, G-Zyme G990, G-Zyme G995, G-Zyme G997, G-Zyme G998, HTAA, Optimax 7525, Purastar OxAm, Purastar ST, Spezyme AA, Spezyme Alpha, Spezyme BBA, Spezyme Delta AA, Spezyme DBA, Spezyme Ethyl, Spezyme Fred (GC521), Spezyme HPA, Spezyme Extra, and Ultraphlow (all from Genencor); Validase HT340L, Valley Thin 340L (all from Valley Research); Avizyme 1500, Dextro 300 L, Kleistase, Maltazyme, Maxamyl, Thermozyme, Thermatex, Starzyme HT 120 L, Starzyme Super Conc, and Ultraphlo.

The present invention also relates to:

The use, in feed for animals of the subfamily Bovinae, of an amylase having an amino acid sequence which has at least 65% identity with amino acids 1-481 of SEQ ID NO: 2;

the use of such amylase in the preparation of a composition for use in a feed for animals of the subfamily Bovinae;

feed additive compositions comprising such amylase, together with at least one additional ingredient selected from vitamins and/or minerals; and a composition (e.g. a feed composition) comprising such amylase together with at least one additional ingredient selected from hay, forage, roughage, and/or feed concentrate.

Preferably, the use in feed is (i) for improving milk yield, weight gain, and/or Feed Conversion Ratio; (ii) for improving milk yield, apparent digestibility, and/or disappearance of feedstuff dry matter using the nylon bag method; (iii) in combination with cellulase. The use of (iii) may be (iv): for improving milk yield and/or back fat thickness.

Preferably, the feed additive comprises a cellulase. More preferably the feed additive is a premix, such as a mineral premix, a vitamin premix, or a premix including vitamins as well as minerals.

The feed composition preferably further comprises a cellulase. The feed composition may be an amylase-enriched concentrate, an amylase-enriched Total Mixed Ration, and/or it may comprise maize and/or sorghum, preferably maize.

The invention also relates to a method of preparing a composition for use in a feed for animals of the subfamily Bovinae, the method comprising the step of adding to at least one feed ingredient an amylase having an amino acid sequence which has at least 65% identity with amino acids 1-481 of SEQ ID NO: 2. Preferably, the method further comprises the addition of a cellulase.

The invention also relates to a method for increasing milk yield of animals of the subfamily Bovinae, the method comprising the step of adding to the feed of the animal an amylase having an amino acid sequence which has at least 65% identity with amino acids 1-481 of SEQ ID NO: 2. Preferably, the method further comprises adding a cellulase to the feed of the animal.

The invention also relates to a method for increasing back fat thickness of animals of the subfamily Bovinae, the method comprising the step of adding to the feed of the animal an amylase having an amino acid sequence which has at least 65% identity with amino acids 1-481 of SEQ ID NO: 2, in combination with a cellulase.

The invention also relates to methods for improving apparent digestibility, disappearance of feedstuff dry matter using the nylon bag method, increasing weight gain and/or improving Feed Conversion Ratio of animals of the subfamily Bovinae, the method comprising the step of adding to the feed or a feed ingredient an amylase having an amino acid sequence which has at least 65% identity with amino acids 1-481 of SEQ ID NO: 2.

The degree of identity between an amino acid sequence of the present invention ("invention sequence"; e.g. amino acids 1-481 of SEQ ID NO: 2 and a different amino acid sequence ("foreign sequence") is calculated as the number of exact matches in an alignment of the two sequences, divided by the length of the "invention sequence" or the length of the "foreign sequence", whichever is the shortest. The result is expressed in percent identity.

As an example, this is part of an alignment of amino acids 1-481 of SEQ ID NO: 2 ("the invention sequence" with SEQ ID NO: 4 ("the foreign sequence"):

```
SEQ2,1-481   1  AAPFNGTMMQYFEWYLPDDGTLWTKVANEANNLSSLGITALWLPPAYKG  49
                    ||||||||||||:||..|.:::.:|:||...||:|:|:|||:||
SEQ4         1  HHNGTNGTMMQYFEWYLPNDGNHWNRLRSDASNLKDKGISAVWIPPAWKG  50
```

An exact match occurs when the "invention sequence" and the "foreign sequence" have identical amino acid residues in the same positions of the overlap (in the alignment example below this is represented by "I"). The number of exact matches in the example is 28.

The length of a sequence is the number of amino acid residues in the sequence (e.g. the length of the sequence having amino acids 1-481 of SEQ ID NO:2 is 481). In the example, the length of the invention sequence is 49, whereas the length of the foreign sequence is 50.

In the example, the overlap is the amino acid sequence "AAPF-AYKG" of the upper sequence; or the amino acid sequence "HNGT-AWKG" of the lower sequence:

In this example there are no gaps (a gap would have been indicated by "–").

The identity of the two partial sequences shown in the above example accordingly is: (28 (exact matches)/49 (length of the shortest sequence))×100%=57.14%

Accordingly, in a particular embodiment, the percentage of identity of an amino acid sequence of a polypeptide with, or to, amino acids 1 to 481 of SEQ ID NO: 2 is determined by i) aligning the two amino acid sequences using the Needle program, with the BLOSUM62 substitution matrix, a gap opening penalty of 10, and a gap extension penalty of 0.5; ii) counting the number of exact matches in the alignment; iii) dividing the number of exact matches by the length of the shortest of the two amino acid sequences, and iv) converting the result of the division of iii) into percentage.

In preferred embodiments, the amylase has an amino acid sequence which has at least 66, 67, 68, or at least 69% identity with amino acids 1-481 of SEQ ID NO: 2. In other preferred embodiments, the amylase has an amino acid sequence which has at least 70, 75, 80, or at least 85% identity with amino acids 1-481 of SEQ ID NO: 2. In still further preferred embodiments, the amylase has an amino acid sequence which has at least 90, 92, 95, 97, or at least 99% identity with amino acids 1-481 of SEQ ID NO: 2.

In alternative embodiments, the amylase has an amino acid sequence which has at least 60, 61, 62, 63, or at least 64% identity with amino acids 1-481 of SEQ ID NO: 2.

In what follows, the amylases having a specified % identity (e.g. at least 65% identity) with amino acids 1-481 of SEQ ID NO: 2 are referred to as homologous amylases.

Non-limiting examples of homologous amylases are:

Amylases derived from *Bacillus amyloliquefaciens*, such as Swissprot entry name AMY_BACAM, primary accession number P00692 (SEQ ID NO: 7), and the commercial amylase sold by Novozymes A/S under the tradename of BAN;

Amylases derived from *Bacillus licheniformis*, such as Swissprot entry name AMY_BACLI, primary accession number P06278 (SEQ ID NO: 8), and the commercial amylase sold by Novozymes A/S under the tradename of DURAMYL;

Amylases derived from *Bacillus* sp., such as the commercial amylase sold by Novozymes A/S under the tradename of STAINZYME;

Amylases derived from *Bacillus* halmapalus, such as the commercial amylase sold by Novozymes A/S under the tradename of NATALASE; and Amylases derived from *Bacillus stearothermophilus*, such as Swissprot entry name AMY_BACST, primary accession number P06279 (SEQ ID NO: 9), and the commercial amylase sold by Novozymes A/S under the tradename of TERMAMYL SC.

Additional non-limiting examples of homologous amylases are:

Amylases having, comprising or consisting of amino acids 1-481, 1-484, 1-486, or 1-513 of SEQ ID NO: 2 (where "1" refers to the starting amino acid of the mature peptide, Ala, cf. the sequence listing);

Amylases having, comprising or consisting of amino acids 1-483 of SEQ ID NO: 4;

Amylases having, comprising or consisting of amino acids 1-483 of SEQ ID NO: 5;

Amylases having, comprising or consisting of amino acids 1-481 of SEQ ID NO: 6 (where "1" refers to the starting amino acid of the mature peptide, Val, cf. the sequence listing);

Amylases having, comprising or consisting of amino acids 1-483 of SEQ ID NO: 7 (where "1" refers to the starting amino acid of the mature peptide, Val cf. the sequence listing);

Amylases having, comprising or consisting of amino acids 1-483 of SEQ ID NO: 8 (where "1" refers to the starting amino acid of the mature peptide, Ala, cf. the sequence listing); and Amylases having, comprising or consisting of amino acids 1-515 of SEQ ID NO: 9 (where "1" refers to the starting amino acid of the mature peptide, Ala, cf. the sequence listing);

as well as fragments or variants of any of the above specified amylases which retain amylase activity.

A fragment is a polypeptide having one or more amino acids deleted from the amino and/or carboxyl terminus. Preferably, a fragment contains at least 450 amino acid residues, more preferably at least 460 amino acid residues, even more preferably at least 470 amino acid residues, and most preferably at least 480 amino acid residues. Additional preferred fragments contain at least 481, 483, 484, or at least 513 amino acid residues. Examples of enzymatically active fragments of the amylase of SEQ ID NO: 2 are the sequences having amino acids 1-481, 1-484, and 1-486 thereof.

A variant may be a conservative variant comprising a conservative substitution, deletion, and/or insertion of one or more amino acids, e.g. small insertions of substitutions that do not significantly affect the folding and/or activity of the protein; small deletions, typically of one to about 30 amino acids; small amino- or carboxyl-terminal extensions, such as an amino-terminal methionine residue; a small linker peptide of up to about 20-25 residues; or a small extension that facilitates purification by changing net charge or another function, such as a poly-histidine tract, an antigenic epitope or a binding domain. Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine).

Non-limiting examples of conservative variants of the amylases of the invention include small amino-terminal insertions (extensions), e.g. of 1 or 2 amino acid residues, such as Ala, or Ala-Ala.

Alternatively, a variant may incorporate amino acid changes of such a nature that the physico-chemical properties of the polypeptides are altered. For example, amino acid changes may improve the thermal stability of the polypeptide, alter the substrate specificity, change the pH optimum, and the like.

The total number of amino acid substitutions, deletions and/or insertions in any of the above-mentioned amino acid sequences is 40, 38, 36, 35, 32, 30, 25, 20, or 15—at most. Preferably the total number of substitutions, deletions and/or insertions is at most 10, preferably 9, more preferably 8, more preferably 7, more preferably at most 6, more preferably at most 5, more preferably 4, even more preferably 3, most preferably 2, and even most preferably 1.

In a particular embodiment, the amylase for use according to the invention is pelleting stable, and/or thermostable. The melting temperature (Tm) of an enzyme is a measure of its thermostability. The amylase of the invention may have a Tm of at least 75° C., 76° C., 77° C., 78° C., 79° C., 80° C., 81° C., 82° C., 83° C., 84° C., 85° C., 86° C., 87° C., 88° C., 89° C., 90° C., 91° C., 92° C., 93° C., 94° C. or at least 95° C., as determined by Differential Scanning Calorimetry (DSC). The DSC is performed in a 10 mM sodium phosphate, 50 mM sodium chloride buffer, pH 7.0. The scan rate is constant, e.g. 1.5° C./min. The interval scanned may be from 20 to 100° C. Another buffer may be selected for the scanning, e.g. a buffer of pH 5.0, 5.5, 6.0, or pH 6.5. In further alternative embodiments, a higher or lower scan rate may be used, e.g. a lower one of 1.4° C./min, 1.3° C./min, 1.2° C./min, 1.1° C./min, 1.0° C./min, or 0.9° C./min.

In another preferred embodiment, the amylase for use according to the invention has an activity at pH 7.0 and 37° C. of at least 35% relative to the activity at the pH-optimum and 37° C. More preferably, the activity at pH 7.0 and 37° C. is at least 40, 45, 50, 55, 60, 65, 70, or at least 75% of the activity at the pH-optimum and 37° C. (cf. Table 6 of Example 6).

In another preferred embodiment, the amylase of the invention has an activity at pH 7.0 and 37° C. and in the presence of 5 mM bile salts of at least 25% relative to the activity at the pH-optimum and 37° C. in the absence of bile salts. More preferably, the activity at pH 7.0 and 37° C. and in the presence of 5 mM bile salts is at least 30, 35, 40, 45, 50, 55, 60, or at least 65% of the activity at the pH-optimum and 37° C. in the absence of bile salts (cf. Table 7 of Example 6).

In a still further preferred embodiment, the specific activity of the amylase of the invention, at pH 7.0 and 37° C., is at least 10%, more preferably at least 15, 20, 25, 30, 35, 40, 45, 50, 55, 60, 65, or at least 70%, relative to the specific activity of the amylase of TERMAMYL SC at pH 5.0 and 37° C. (cf. Table 8 of Example 6).

In another preferred embodiment, the specific activity of the amylase of the invention, at pH 7.0 and 37° C. and in the presence of 5 mM bile salts, is at least 10%, more preferably at least 15, 20, 25, 30, 35, 40, 45, 50, 55, 60, 65, 70, or at least 75%, relative to the specific activity of the amylase of TERMAMYL SC at pH 5.0 and 37° C. and in the presence of 5 mM bile salts (cf. Table 9 of Example 6).

The activities referred to in the above preferred embodiments may suitably be determined using a reducing sugar assay, e.g. as described in Example 6, using preferably waxy corn as a substrate. A detailed procedure is described in Example 6.

In another particular embodiment, the amylase for use according to the invention is stable in the presence of protease. Examples of proteases are digestive proteases, and feed proteases such as the proteases described in, e.g., WO 01/58275, WO 01/58276, WO 2004/111220 2004/111221, WO 2004/072221, and WO 2005/035747. Examples of digestive proteases are pancreatin and pepsin. The protease stability may be determined by incubating 0.5 mg purified amylase enzyme protein/ml in a buffer at a desired pH (e.g. pH 3, 4, or 5), for the desired time (e.g. 30, 45, 60, 90, or 120 minutes) in the presence of protease (e.g. pepsin, 70 mg/l), and then raising pH to the desired pH (e.g. pH 4, 5, 6, or 7) and measuring residual activity using e.g. the reducing sugar assay of Example 6 herein. The residual amylase activity is preferably at least 20%, preferably at least 30, 40, 50, 60, 70, 80, or at least 90% relative to the control (a non-protease-treated sample).

The amylase of the invention may be used in combination with a cellulase. The term "in combination with" in particular includes cases where the two enzymes are active and excert their effect simultaneously or overlapping in time, preferably simultaneously, but it may also include action of the enzymes one-by-one.

In the present context, a cellulase is an enzyme that catalyzes the endohydrolysis of 1,4-beta-D-glucosidic linkages in cellulose, lichenin and cereal beta-D-glucans. Other names are, e.g., endo-1,4-beta-D-glucanase; beta-1,4-glucanase; and beta-1,4-endoglucan hydrolase. The systematic name is 1,4-(1,3; 1,4)-beta-D-glucan 4-glucanohydrolase. In a preferred embodiment the cellulase of the invention is, or can be, classified as EC 3.2.1.4 (Enzyme Nomenclature 1992, see above).

Cellulase activity may be determined by any suitable assay. Generally, assay-pH and assay-temperature may be adapted to the enzyme in question. Examples of assay-pH-values are pH 2, 3, 4, 5, 6, 7, 8, 9, 10, 11, or 12. Examples of assay-temperatures are 30, 35, 37, 40, 45, 50, 55, 60, 65, 70, 80, 90, or 95° C. Preferred pH values and temperatures are in the physiological range, such as pH values of 3, 4, 5, 6, 7, or 8, and temperatures of 30, 35, 37, or 40° C.

A preferred cellulase is derived from a strain of *Trichoderma*, preferably *Trichoderma reseei*, more preferably the CELLUCLAST cellulase (or a cellulase component thereof) which is commercially available from Novozymes A/S. Examples of cellulase components are cellobiohydrolase I and II (CBHI, CBHII), as well as endoglucanase I and II (EGI, EGII). The term "derived from" is interpreted as described in the above (amylase section) and includes wild-type cellulases, as well as variants and fragments thereof.

In the present context, an animal of the subfamily Bovinae (also called bovines, or bovine animals) means an animal of the kingdom of Animalia, the phylum of Chordata, the class of Mammalia, the order of Artiodactyla, and the family of Bovidae.

This biological subfamily includes about 24 species of medium-sized to large ungulates, including domestic cattle, Bison, the Water Buffalo, the Yak, and the four-horned and spiral-horned antelopes. General characteristics include a cloven-hoof and usually at least one of the sexes of a species having a true horn.

Preferred genera include *Tetracerus*, *Boselaphus*, *Bubalus*, *Bos*, *Pseudoryx*, *Syncerus*, *Bison*, *Tragelaphus*, and *Taurotragus*. A most preferred genera is *Bos*, which includes the species of Aurochs (*Bos primigenius*, extinct), Banteng (*Bos javanicus*), Gaur (*Bos frontalis*), Yak (*Bos mutus*), Domestic Cattle (*Bos taurus*, *Bos indicus* (today often counted as *B. primigenius*), and Kouprey (*Bos sauveli*). For the present purposes, Domestic cattle are the most preferred species. For the present purposes the term includes all races of domestic cattle, and all production kinds of cattle, in particular dairy cows and beef cattle.

Bovines are ruminants, which are characterised by having additional fermentation capacity compared to mono-gastric animals. For example, cows and sheep have three fore-stomachs before the abomasum. The functionally most important is the rumen, which serve as a chamber for feed storage and fermentation. The fermentative processes are carried out by a large and complex flora of anaerobic microorganisms (bacteria, protozoa and fungi). These can degrade cell wall material in addition to protein and starch, thus allowing the ruminant animal to ingest and benefit from feed material that is otherwise not degraded in the abomasum or small intestine. This includes for example hay, other forages and silages rich in cell wall material.

The products of the fermentation in the rumen are short-chain fatty acids (SCFA), which serve as a primary energy source in ruminants, and gasses such as methane and carbon dioxide. In in vitro rumen systems, the volume of gas production is therefore often taken as a measure of the fermentability of a given feed, and an increased gas production in vitro is taken as a measure of improved feed degradation and increased energy availability. Most in vitro systems include the use of freshly sampled rumen fluid, typically from sheep or cows.

Optimal milk production requires sufficient energy intake and thus preferably good feed utilisation by dairy cows. The same is true for obtaining optimal weight gain of beef cattle.

It is contemplated that the amylases for use according to the invention improve the degradation in the rumen of dietary starch, in particular slowly degradable starch (such as maize starch that is not heat-treated and/or contains large particles, or potato starch), thereby contributing more energy to the rumen microorganisms and to the ruminant itself (in the form of short-chain fatty acids).

It is also contemplated, that the amylases for use according to the invention improve the degradation in the small intestines of by-pass starch (i.e. starch which passes the rumen and reaches the small intestines) and/or increase the glucose absorption, thus salvaging energy by minimising the microbial degradation in the large intestine and excretion of starch in the faeces.

It is contemplated, that the observed improved degradation of starch will give more energy to the bovines and thus increase milk yield or weight gain.

In a particular embodiment of the use of a bacterial amylase of the invention, by reference to Example 2 herein, the average gas production (GP) is at least 0.9 ml, using the modified HFT method of Example 1 herein and using TMR as a substrate. This is whatever the dose of the amylase, preferably in an optimum dose, determined using the same method.

In preferred embodiments, the average gas production (determined as described above) is at least 1.0, 1.5, 2.0, 2.5, 3.0, or at least 3.5 ml.

As it can be seen from Example 2, the fungal amylases gave rise to a gas production well below 0.9 ml. This means that the fungal amylases apparently do not cause starch to disappear in the rumen. This observation is confirmed by Tricarico et al (Animal Science 2005, 81: 365-374) who observed the same in lactating dairy cows and ruminally cannulated steers the feed of which was supplemented with AMAIZE (see the abstract).

That the observed increased gas production by the bacterial amylases of the invention actually translates into an improved degradation of starch can be seen from Example 4.

Thus, in a particular embodiment, by reference to Example 4, the bacterial amylases for use according to the invention are capable of reducing the amount of residual starch, using the modified HFT method of Example 1 with TMR as a substrate and incubating for 4 hours, as compared to a control without exogenous amylase. The residual starch may be determined as described in Example 4.

In another particular embodiment, the bacterial amylases for use according to the invention at least partially degrade starch already in the rumen of bovine animals.

The at least 0.9 ml average gas production referred to above translates into a degradation of at least 5% of the starch present in the substrate. Accordingly, the bacterial amylase for use according to the invention preferably degrades at least 5% (w/w) of the starch in the substrate (or diet, or feed composition), more preferably at least 6, 7, 8, 9, 10, 11, 12, 13, 14 or at least 15% of the starch, the latter percentage corresponding to 1.8 ml average gas production. In additional preferred embodiments, the amylase degrades at least 20, 22, 24, 26, 28 or at least 30% of the starch. A preferred substrate is TMR, e.g. as described in Example 1.

For the present purposes, an improved milk yield means either of the following: (i)

An increased volume of milk production per day (l/day); (ii) an increased weight of milk production per day (kg/day); (iii) an increased ratio of kg milk produced relative to dry matter intake in kg per day (kg milk/kg DMI); (iv) an increased weight of milk fat produced per day (kg/day); (v) an increased weight of milk protein produced per day (kg/day); (vi) an increased production of 3.5% fat corrected milk per day (kg/day); and/or (vii) an increased production of milk solids per day, wherein the term "milk solids" includes the total amount of lactose, fat, protein, and lactose. An increased milk yield may also manifest itself as (viii) an increased weight of lactose produced per day (kg/day), or (ix) an increased 4% fat corrected milk per day (kg/day), e.g. calculated as follows: (0.4×kg milk yield)+(15×kg of milk fat).

An increased milk yield is obtained, e.g., when the dry matter content of the milk increases (e.g. more fat or protein) without a concomitant volume increase, when the volume increases without an increase in the dry matter, and when the volume, as well as the dry matter content of the milk increases.

In particular embodiments, by reference to Example 7 herein, (a) the daily milk production (kg/day) is increased by at least 1%, preferably 2, 3, 4, 5, 6, 7, 8, or at least 9%, relative to a control without added amylase;
(b) the ratio of daily milk production (kg/day) relative to dry matter intake (DMI) (kg/day) (kg milk/kg DMI) is improved, relative to a control without added amylase, by at least 1%, preferably by at least 2, 3, or at least 4%;
(c) the weight of milk fat produced per day (kg/day) is improved, relative to a control without added amylase, by at least 1%, preferably by at least 2, 3, 4, 5, 6, 7, or at least 8%;
(d) the weight of milk protein produced per day (kg/day) is improved, relative to a control without added amylase, by at least 1%, preferably by at least 2, 3, 4, 5, 6, 7, 8, or by at least 9%;
(e) the production of 3.5% (or 4%) fat corrected milk per day (kg/day) is improved, relative to a control without added amylase, by at least 1%, preferably by at least 2, 3, 4, 5, 6, 7, 8, or by at least 9%; and/or
(f) the production of 3.5% (or 4%) fat corrected milk (kg/day) is improved, relative to a control without added amylase, by at least 1%, preferably by at least 2, 3, 4, or by at least 5%.

Embodiments (a)-(f) preferably refer to a cow trial as described in the below FCR-paragraph.

The Feed Conversion Ratio (FCR) is indicative of how effectively a feed is utilized. The lower the FCR, the better the feed is utilized. The FCR may be determined on the basis of a cow trial comprising a first treatment in which the amylase for use according to the invention is added to the animal feed in a desired concentration (e.g., 6 or 30 mg enzyme protein per kg feed, preferably per kg feed dry matter (DM)), and a second treatment (control) with no addition of the amylase to the animal feed, each treatment consisting of four, or seven, cows, preferably dairy cows, the cows being housed in a barn, preferably with free stalls, equipped with Calan gates for the measurement of individual feed intake, the cows being fed a TMR diet, preferably containing 50% concentrate (mainly composed of corn meal, wheat middlings, distiller's dried grain with solubles, and soy bean meal (SBM)), 37% corn silage, 7% alfalfa haylage, and 6% alfalfa hay, the FCR being calculated as the feed intake in kg/cow (preferably kg DM/cow) relative to milk yield (or alternatively weight gain) in kg per day and cow (alternatively kg per cow, for weight gain) for a desired period of the trial (e.g. the first, the second, the third, or the fourth 21-days periods, or the whole 84-days period), the FCR for the first treatment being improved relative to the FCR of the second treatment. For further details, see Example 7. In particular embodiments, the FCR is improved (i.e., reduced) as compared to the control by at least 1.0%, preferably at least 1.5%, 1.6%, 1.7%, 1.8%, 1.9%, 2.0%, 2.1%, 2.2%, 2.3%, 2.4%, or at least 2.5%. In further particular embodiments, the FCR is improved (i.e. reduced) as compared to the control by at least 2.6%, 2.7%, 2.8%, 2.9%, or at least 3.0%. In still further particular embodiments, the FCR is improved (i.e., reduced) as compared to the control by at least 3.1%, 3.2%, 3.3%, 3.4%, 3.5%, 3.6%, 3.7%, or at least 3.8%. In the alternative, the improvement is relative to a control group receiving the AMAIZE amylase in a dosage of 240 DU/kg TMR dry matter.

An improved weight gain means an improved daily, weekly, bi-weekly, or monthly weight gain (in g or kg per the relevant time period), relative to a control without added amylase. This is preferably determined in a trial as described in the above FCR-paragraph.

In a particular embodiment, the amylase of the invention improves the apparent digestibility of the feed (e.g., as compared to a control without amylase). In particular, the amylase of the invention improves dry matter digestibility, neutral-detergent fibre digestibility, and/or organic matter digestibility. The amylase of the invention may furthermore improve the starch digestibility, and/or the crude protein digestibility. For example, the amylase of the invention improves (i) dry matter digestibility by at least 1%, more preferably by at least 2, 3, 4, 5, 6, 7, 8, or by at least 9%; (ii) neutral-detergent fibre digestibility by at least 2%, more preferably by at least 4, 5, 10, or by at least 20%, even more preferably by at least 25, 30 or by at least 35%; (iii) organic matter digestibility by at least 1%, more preferably by at least 2, 3, or by at least 4%, even more preferably by at least 5, 6, or by at least 7%; (iv) starch digestibility by at least 1%, more preferably by at least 2%; and/or (v) crude protein digestibility by at least 1%, more preferably by at least 2, 3, 4, 5, or at least 6%.

The apparent digestibility as outlined above may be determined on the basis of a cow trial comprising a first treatment in which the amylase for use according to the invention is added to the animal feed in a desired concentration (e.g., 6 or 30 mg enzyme protein per kg feed), and a second treatment (control) with no addition of the amylase to the animal feed, each treatment consisting of six cows, e.g. male or female, preferably dairy cows, the cows being housed in a barn, preferably with free stalls, equipped with Calan gates for the measurement of individual feed intake, the cows being fed a TMR diet, preferably containing 50% concentrate (mainly composed of corn meal, wheat middlings, distiller's dried grain with solubles, and soy bean meal (SBM)), 37% corn silage, 7% alfalfa haylage, and 6% alfalfa hay, in an amount corresponding to average daily intake in the last week of period 4 (of four 21-days periods) for 8 additional days, collecting, from days 5 through 8, fecal grab samples (of approximately 300 g) via rectal palpation every 8 h (preferably the sampling point in time was increased by 1 hr each day) until a total of 12 samples were collected for each cow, taking samples of TMR (from each group) and orts (for each cow) daily, pooling all fecal, TMR, and orts samples (respectively, for each cow) together, drying for 48 h in a 60° C. forced air oven, grinding samples through a 1-mm screen, analyzing for dry matter (DM), acid detergent fibre (ADF) and neutral detergent fibre (NDF), e.g. as described by Goering, H. K., Van Soest, P. J., 1970, in Agriculture Handbook No. 379, analyzing the samples for nitrogen (N) (e.g. using Elementor Vario Max CN Analyzer), and for ash content (600° C. in a muffle furnace for 5 h), using indigestible NDF as a marker to calculate apparent digestibility from the total tract. Preferably, indigestible NDF is determined after 120 hr of in vitro rumen incubation (Goering and Van Soest, 1970) using a Daisy-II incubator (Ankom Technology, Macedon, N.Y., US) and rumen fluid from a cow fed the control diet. For further details see Example 8 and Table 11.

In another particular embodiment, the amylase of the invention improves the total tract apparent digestibility of crude fibre, crude protein, organic matter, and/or crude fat (e.g., as compared to a control without amylase). For example, the amylase of the invention improves the apparent digestibility of (i) crude fibre by at least 1%, more preferably by at least 2, or by at least 3%; (ii) crude protein by at least 1%; (iii) organic matter by at least 1%, more preferably by at least 2 or by at least 3%; and/or (iv) crude fat by at least 1%, more preferably by at least 2, 3, 4, or by at least 5%.

The total tract apparent digestibilities may be determined on the basis of an in vivo cow study with three non lactating cows (German Holstein), and two treatments, namely the addition of 50 mg enzyme protein (EP) per kg dry matter (DM), and a control without enzyme. The enzyme is added to the daily ration. (e.g. TMR consisting of 44% corn silage, 18% grass silage, 9% hay and 29% corn based concentrate). The cows are preferably kept in an air conditioned tied-up barn (20° C.) on rubber mats with individual feeding and free access to water. The experiment may last for 2 periods of 25 days each (in total 50 days); in each period the first 14 days were used for adaptation and the following 11 days for sampling. Each cow is preferably fed 5.5 kg (DM) TMR per day at 7:00 h and 16:00 h and 0.5 kg (DM) hay two hours after the morning feeding. In addition 100 g/d of a mineral premix is preferably administered. From days 22 through 25, fecal grab samples (of approximately 200 g) are collected via rectal palpation at 8:30 h from each cow. $TiO_2$ may be used as a marker to calculate apparent digestibility from the total tract. As is usual in the art, DM may be determined by drying at 105° C. until no further weight loss, normally for 24 hours. For further details, see Example 9 and Table 16.

In a still further embodiment, the amylase of the invention improves the dry matter (DM) disappearance from feedstuffs during incubation in nylon bags, e.g. from feedstuffs such as corn grain, barley, corn silage, and/or TMR. For example, the DM disappearance from corn grain, barley, corn silage, and TMR after an incubation time of 2 hours is at least 1% (preferably at least 5, 10, 15, 20, 25, 30 or at least 35%), at least 1% (preferably at least 2, 4, 6, 8 or at least 10%), at least 1% (preferably at least 2, or at least 3%), and at least 1% (preferably at least 2, or at least 3%), respectively. As another example, the DM disappearance from corn grain, barley, corn silage, and TMR after an incubation time of 4 hours is at least 1% (preferably at least 5, 10, 15, 20, 25, or at least 26%), at least 1% (preferably at least 2, 4, or at least 6%), at least 1% (preferably at least 2, or at least 3%), and at least 1% (preferably at least 2, or at least 3%), respectively. As a still further example, the DM disappearance from corn grain and barley after an incubation time of 8 hours is at least 1% (preferably at least 5, 10, 15, 20, 25, 30 or at least 33%), at least 1% (preferably at least 2%), respectively.

The feedstuff dry matter disappearance may be determined in an in vivo trial as described above (under total tract apparent digestibility), and using the well-known nylon bag technique which is referenced and described in more detail in Example 9. For further details, see Example 9 and Tables 12-15.

In still further embodiments, the amylase of the invention in combination with cellulase (i) improves milk yield (kg/d), preferably in the early lactation phase (e.g. from day 1 through 14 after parturition), more preferably without changes in milk composition; and/or (ii) improves the back-fat thickness, preferably on or after day 140 after parturition. The milk yield and back-fat thickness may be determined in a 9 months in vivo feeding trial using two groups, each consisting of e.g. 220 dairy cows (German Holstein). The cows are preferably housed in a cubicle barn with slotted floors. The experimental period preferably includes three weeks before and 20 weeks after parturition. Cows are fed (preferably eight times a day) a Total Mixed Ration (TMR) that is either not enzyme-supplemented (control) or supplemented with a suitable dose of the enzymes (e.g. amylase corresponding to 25 mg enzyme protein (EP)/kg TMR dry matter (DM), and 1.4 ml/kg TMR of cellulase, or a similar amount (EP/kg) as for the amylase). The enzymes may be sprayed onto the TMR immediately before feeding. The main components of the TMR are corn silage, grass silage and concentrate (which may be mixed on the farm), and the dry matter content may be approximately 50%. The cows are preferably milked 3 times daily in a rotary milking parlour. The individual milk yield and composition as well as the thickness of the back fat are assessed regularly during the trial. For further details, see Example 10 and FIGS. 1 and 2.

For the present purposes, the terms feed and fodder are considered synonymous. As regards feed compositions for bovines such as cows, as well as ingredients thereof, the bovine diet is usually composed of an easily degradable fraction (named concentrate) and a fibre-rich less readily degradable fraction (named hay, forage, or roughage).

Hay is made of dried grass, legume or whole cereals. Grasses include among others timothy, ryegrasses, fescues. Legumes include among others clover, lucerne or alfalfa, peas, beans and vetches. Whole cereals include among others barley, maize, oat, sorghum. Other examples of whole cereals are wheat and rye. For the present purposes the terms maize and corn are considered synonymous. Other forage crops include sugarcane, kales, rapes, and cabbages. Also root crops such as turnips, swedes, mangels, fodder beet, and sugar beet (including sugar beet pulp and beet molasses) are used to feed ruminants. Still further crops are tubers such as potatoes, cassaya and sweet potato. Silage is an ensiled version of the fibre-rich fraction (e.g. from grasses, legumes or whole cereals, the total plant or only part thereof, e.g. maize) whereby material with a high water content is treated with a controlled anaerobic fermentation process (naturally-fermented or additive treated).

Concentrate is largely made up of cereals (such as barley including brewers grain and distillers grain, maize, wheat, sorghum, oats, and/or rye), but also often contain protein-rich feed ingredients such as soybean (preferably soybean meal), rapeseed, palm kernel, cotton seed and sunflower.

Cows may also be fed total mixed rations (TMR), where all the dietary components, e.g. forage, silage concentrate, and premixes (e.g. minerals, vitamins) are mixed before serving.

By reference to Example 3, in a particular embodiment the feed composition of the invention includes TMR, concentrate, maize, barley, rye, wheat, oat, and/or potatoes. In a preferred embodiment the feed composition comprises at least one of maize and sorghum (or includes maize and/or sorghum), most preferably maize. Terms like "maize", "barley", "potatoes" etc. include whole plants and parts thereof, as well as various preparations and substances derived therefrom, including among others leaves, flowers, stalks, roots, fruits, kernels, grain, meal, and starch. Furthermore, these plant parts may be used as such (in natural form), dried, crushed, soaked, or as silage (non-limited list).

In further particular embodiments, the feed composition of the invention is an amylase-enriched concentrate or an amylase-enriched Total Mixed Ration (TMR), wherein the amylase is a bacterial amylase for use according to the invention, as described hereinabove. The concentrate may be pelleted, and the amylase may be added before or after pelleting. The concentrate may also be a mash-concentrate. The amylase for use according to the invention may furthermore be added to any other feed ingredient or composition, e.g. admixed, or as a top-dressing, or it may be included in a feed additive, for example via a premix as described below.

The feed additive composition of the invention comprises, in addition to the amylase for use according to the invention as described hereinabove, at least one additional ingredient selected from amongst vitamins and minerals. For example, the feed additive of the invention may include (i) at least one vitamin, (ii) at least one mineral, or (iii) at least one vitamin and at least one mineral.

The at least one vitamin may be fat-soluble or water-soluble. Examples of fat-soluble vitamins are vitamin A, vitamin D3, vitamin E, and vitamin K, e.g. vitamin K3. Examples of water-soluble vitamins are vitamin B12, biotin and choline, vitamin B1, vitamin B2, vitamin B6, niacin, folic acid and panthothenate, e.g. Ca-D-panthothenate.

The at least one mineral may be a macro mineral and/or a trace mineral. Examples of trace minerals are manganese, zinc, iron, copper, iodine, selenium, and cobalt. Examples of macro minerals are calcium, phosphorus and sodium.

Premixes are recognized terms in the art for certain feed additives. They may be solid or liquid. A mineral premix is a composition which is intended for addition to animal feed and which comprises desired kinds and amounts of minerals, in particular trace minerals. A vitamin premix is a composition which is intended for addition to animal feed and which comprises desired kinds and amounts of vitamins. Some premixes include both vitamins and minerals. An example of such a combined premix for cows is included in Example 12 herein.

The present invention also relates to the claimed uses, methods, and compositions in which the bacterial amylase of the invention is used in combination with (i) other enzymes for ruminants, such as a protease, a phytase, a cellwall-degrading enzyme such as a xylanase, a cellulase, and/or an endoglucanase; (ii) Rumensin (monensin sodium); and/or (iii) Tylan (tylosin).

The present invention is further described by the following examples which should not be construed as limiting the scope of the invention.

EXAMPLES

Chemicals used as buffers and substrates were commercial products of at least reagent grade.

Example 1

Modified Hohenheim Forage Value Test (HFT)

The Hohenheim Forage value Test (HFT) is described by Menke et al. (1979), J. Agric. Sci. Camb. 93, 217-222: "The estimation of the digestibility and metabolizable energy content of ruminant feedinggstuffs from the gas production when they are incubated with rumen liquor in vitro", by Steingass, H. (1983): "Bestimmung des energetischen Futterwertes von wirtschaftseigenen Futtermitteln aus der Gasbildung bei der Pansensaftfermentation in vitro" Hohenheim Universität, Fak. Agrarwiss. Dissertation, and by Steingass et al. in Tierernährung 14; pp 251-270 (1986): "Schätzung des energetischen Futterwertes aus der in vitro mit Pansensaft bestimmten Gasbildung und der chemischen Analyse. 1. Untersuchungen zur Methode Übers. Its purpose is primarily to estimate the net energy for lactation in feeds for milk production on the basis of gas production.

The present modified version of this test was used for testing the effect of exogenous enzymes in a rumen in vitro system.

In brief, the feed substrate was weighed into a glass syringe together with a composition of rumen liquor and an appropriate mixture of buffers. The glass syringe was closed with a close-fitting but movable piston allowing for the increasing volume of the produced gas. The syringe was incubated at 39° C. for 4 h. The quantity of produced gas was measured and put into a formula for conversion (see the formula in Example 2).

Reagents
Mass Element Solution:
6.2 g potassium dihydrogen phosphate ($KH_2PO_4$)
0.6 g magnesium sulfate heptahydrate ($MgSO_4 \cdot 7H_2O$)
9 ml concentrated phosphoric acid (1 mol/l)
dissolved in aqua dist. ad 1 l (pH about 1.6)
Buffer Solution:
35.0 g sodium hydrogen carbonate ($NaHCO_3$)
4.0 g ammonium hydrogen carbonate (($NH_4$)$HCO_3$)
dissolved in aqua dist. ad 1 l
Trace Element Solution:
13.2 g calciumchloride dihydrate ($CaCl_2 \cdot 2H_2O$)
10.0 g manganese(II) chloride tetrahydrate ($MnCl_2 \cdot 4H_2O$)
1.0 g cobalt(II) chloride hexahydrate ($CoCl_2 \cdot 6H_2O$)
8.0 g iron(III) chloride ($FeCl_3 \cdot 6H_2O$)
dissolved in aqua dist. ad 100 ml
Sodium Salt Solution:
100 mg sodium salt
dissolved in aqua dist. ad 100 ml
Reduction Solution:
First 3 ml sodium hydroxide (c=1 mol/l), then 427.5 mg sodium sulphide hydrate ($Na_2S \cdot H_2O$) were added to 71.25 ml $H_2O$. The solution was prepared shortly before it was added to the medium solution
Enzyme Buffer:
10.88 g sodium acetate trihydrate ($CH_3COONa \cdot 3H_2O$)
5.88 g calciumchloride-dihydrate ($CaCl_2 \cdot 2H_2O$)
0.1 g BSA (bovine serum albumin)
dissolved in aqua dist. ad 2 l, with acetic acid adjusted to pH=5,8
Equipment:
Syringe (glass injection, 100 ml, 1/1 graduated with capillary base)
A silicon tube (for each syringe piece of about 50 mm), which was pulled over the capillary base and can be closed with a clamp
Rotor with power unit for 65 syringes, about 1 rotation per minute
Incubator with ventilator (precision +0.5° C., minimum size inside: 70 cm*70 cm*50 cm)
A precision or analytical balance
Suction pump (e.g. hand-operated, adapted air-pump for motorcycles) to remove the content of rumen, return valve, washing flask
Feeding bottle (2 l) with plug to collect rumen liquor
Gas bottle with technical carbon dioxide and reduction valve
Equipment to fill the rumen liquor, consisting of: a semi automatic pipette (50 ml), a Woulff bottle (2 l), a magnetic stirrer, a thermostat with circulation pump and a PVC-bowl (10 l)
Procedure Substrate: The substrate (feeding stuff) was Total Mixed Ration (TMR) composed of 44% standard-concentrate (commercially available from the University of Hohenheim, Institut für Tierernährung), 6% standard-hay (commercially available from the University of Hohenheim, Institut für Tierernährung), 37% maize silage and 13% grass silage, both dried at 65° C. (both silages were from a farm in Village-Neuf, St. Louis Cedex, France). All ingredients were milled with a lab-mill through a 1.5 mm screen and then mixed to form the TMR.

Sample weighing: Feeding stuff with a dry matter content of 400 mg was weighed exactly into each of 36 syringes. 15 of these syringes were the substrate controls, displaying the gas production without the effect of enzymes. The remaining 21 syringes were needed for the enzyme samples (7 syringes for 1 enzyme sample). Afterwards the piston, which had first been greased with Vaseline, was inserted into the syringe. This applies also to the remaining 28 syringes, which contain the 24 ml of medium solution with rumen liquor, but without any substrate samples. The gas production of 7 syringes represents the mean value of gas production from the rumen liquor alone. The remaining 21 syringes are the enzyme controls without any substrate. When the piston is greased with Vaseline, the frictional resistance of the syringe is reduced. Furthermore, the syringe is water- and airproof. Until the filling with rumen liquor all syringes were retained in an incubator at 39° C.

Preparation of the Medium Solution: the Components were Mixed in the Woulff bottle in following order:
711 ml water
0.18 ml trace element solution
355.5 ml buffer solution
355.5 ml mass element solution The completed solution was warmed up to 39° C. (water bath or PVC-box with thermostat) and was kept homogeneous by a magnetic stirrer. First, 1.83 ml sodium salt solution was added. The whole time the medium solution was fumigated with $CO_2$ by a submerged hose. At 36° C., all of the reduction solution was added. The indicator changed from blue to red to colourless. The rumen liquor was added, when the indicator turned colourless. The $CO_2$-gassing continued, first with a submerged hose for 15 minutes, during the filling of the syringes the hose was lifted to hold the liquid saturated with $CO_2$.

Extraction of the rumen liquor: Before feeding the test animals (mainly fistulated sheep, occasionally cows) in the morning, the rumen liquor was extracted into a preheated 2 l feeding bottle, which was used as a collection vessel. The rumen fluid was sieved using a loosely woven linen bag, gently transferred to the thermo flask and care was taken to exclude air during transport to the laboratory. 750 ml of rumen liquor were added to approximately 1400 ml of medium solution under continued agitation and $CO_2$-gassing.

Filling the syringes: The enzymes to be tested were diluted in a certain relation to the enzyme buffer. The enzyme was added into the corresponding syringe in exactly 0.4 ml solution, whereby the enzyme solution must cover the substrate completely. After the mixture of medium solution and rumen liquor was homogenised, 24 ml were put with a semi-automatic pipette into each syringe, which was warmed up to 39° C. in the incubator before. This represents a volume of 18 ml medium solution and 6 ml rumen liquor. Afterwards, all bubbles were removed by careful shaking. Simultaneously, all feed clumps were broken up this way. After closing the clamp, the exact volume of the liquid without any gaseous phase was registered at the level of the piston. The syringes were put directly into the rotor of a pre-heated incubator (39° C.).

Incubation and determining the gas volume: During incubation the syringes must lie in a horizontal position inside the rotor. The transmission should be adjusted to one rotation per minute. During the incubation, the temperature in the incubator should be kept at 39° C. +0.5° C. After four hours, the incubation was finished. The gas formation was measured by reading carefully the position of the piston at the calibration scale. Furthermore, it was checked by careful turning, that the piston had not got stuck. Through interpolation between two scale lines a reading accuracy of up to +0.5 ml can be reached.

Example 2

Test of Amylases in vitro

A number of bacterial amylases, and for comparison three fungal amylases, were tested in the in vitro ruminant model of Example 1. Each experiment was repeated a number of times ("n").

The following amylases were obtained from Novozymes A/S, Krogshoejvej 36, 2880 Bagsvaerd, Denmark: BAN 240L, STAINZYME 12L, TERMAMYL SC L, NATALASE 200L, DURAMYL 300 L DX, and FUNGAMYL 800L. The VALIDASE BAA and VALIDASE FAA amylases were obtained from Valley Research Inc., 3502 North Olive Road, South Bend, Ind. 46628, US. The AMAIZE amylase was obtained from Alltech (Alltech International Head-quarters, 3031 Catnip Hill Pike, Nicholasville, Ky. 40356, US).

The results are shown in Table 1 below as average Gas Production (GP). The GP is given in absolute figures, as well as in % as compared to a control without addition of exogenous enzymes (ml/%). To correct for the gas produced from the substrate available in the enzyme preparations (e.g. protein and the formulation substances such as glucose or sucrose), enzyme control samples containing enzyme and rumen fluid but not the feed substrate were incubated in the HFT system. The effect of the enzymes on the feed substrate (Delta-G) was calculated as follows, essentially as suggested by Wallace et al in J. Anim. Sci. 2001, 79:1905-1916: Delta-G=(SE−SC)−(RFE−RFC), where SE=rumen fluid, feed substrate and enzyme, SC=rumen fluid and feed substrate, RFE=rumen fluid and enzyme, and RFC=rumen fluid.

In Table 1, the dose of each of the amylases is indicated as crude protein (CP) in mg per kg of substrate, and as enzyme protein (EP) in mg per kg of substrate.

Crude protein (CP) was measured by a combustion method where mainly $CO_2$, $H_2O$, $NO_x$ and $N_2$ are passed through different sorts of filters to exclude all but nitrogen, which is then measured, in a helium carrier, by a thermal conductivity cell. A LECO FP-528 Nitrogen analyzer was used for this purpose, according to the manufacturer's instructions. Crude protein is calculated as nitrogen (N) multiplied by a factor 6.25, i.e. Crude protein (g/kg)=N (g/kg)×6.25. The nitrogen content may also be determined by the Kjeldahl method (A.O.A.C., 1984, Official Methods of Analysis 14th ed., Association of Official Analytical Chemists, Washington D.C.).

Enzyme protein (EP) was determined on the basis of the enzyme activity and the specific activity of the enzyme in question, by reference to the alpha-amylase assay of Example 5.

TABLE 1

| | | Enzyme dose per kg of substrate | | | |
|---|---|---|---|---|---|
| Enzyme | Origin | mg protein (CP) | mg enzyme protein (EP) | n | Average GP (ml/%) |
| Bacterial amylases | | | | | |
| BAN 240L | Bacillus amyloliquefaciens | 983 | 500 | 3 | 1.2/5.1 |
| STAINZYME 12L | Bacillus sp. | 311 | 115 | 2 | 0.9/3.8 |
| STAINZYME 12L | Bacillus sp. | 933 | 345 | 2 | 1.7/6.6 |
| STAINZYME 12L | Bacillus sp. | 3108 | 1149 | 5 | 2.7/11.2 |
| TERMAMYL SC L | Bacillus stearothermophilus | 33 | 9 | 7 | 1.6/6.3 |
| TERMAMYL SC L | Bacillus stearothermophilus | 100 | 28 | 15 | 1.9/7.8 |
| TERMAMYL SC L | Bacillus stearothermophilus | 217 | 60 | 2 | 2.7/12.7 |
| TERMAMYL SC L | Bacillus stearothermophilus | 417 | 115 | 1 | 3.0/14.6 |
| TERMAMYL SC L | Bacillus stearothermophilus | 836 | 230 | 2 | 3.0/13.9 |
| TERMAMYL SC L | Bacillus stearothermophilus | 1000 | 275 | 10 | 3.2/11.2 |
| TERMAMYL SC L | Bacillus stearothermophilus | 1671 | 460 | 1 | 2.8/12.4 |
| NATALASE 200L | Bacillus halmapalus | 73 | 52 | 1 | 1.6/7.1 |
| NATALASE 200L | Bacillus halmapalus | 218 | 156 | 1 | 2.1/9.3 |
| NATALASE 200L | Bacillus halmapalus | 471 | 338 | 2 | 2.9/12.7 |
| NATALASE 200L | Bacillus halmapalus | 906 | 650 | 1 | 2.7/11.2 |
| NATALASE 200L | Bacillus halmapalus | 1813 | 1301 | 2 | 3.2/12.1 |
| NATALASE 200L | Bacillus halmapalus | 3626 | 2602 | 1 | 2.0/6.4 |
| NATALASE 200L | Bacillus halmapalus | 7252 | 5204 | 1 | 2.7/8.8 |
| DURAMYL 300L DX | Bacillus licheniformis | 186 | 217 | 3 | 0.9/3.6 |
| DURAMYL 300L DX | Bacillus licheniformis | 559 | 480 | 2 | 1.7/6.1 |
| DURAMYL 300L DX | Bacillus licheniformis | 1863 | 1600 | 4 | 3.7/14.5 |
| VALIDASE BAA | Bacillus subtilis | 1000 | — | 4 | 1.9/6.2 |
| VALIDASE HT | Bacillus subtilis | 1000 | — | 4 | 2.3/7.5 |
| Fungal amylases | | | | | |
| FUNGAMYL 800 L | Aspergillus oryzae | 814 | 670 | 2 | 0/0 |
| VALIDASE FAA | Aspergillus oryzae | 1000 | — | 2 | 0.2/0.7 |

TABLE 1-continued

| Enzyme | Origin | mg protein (CP) | mg enzyme protein (EP) | n | Average GP (ml/%) |
|---|---|---|---|---|---|
| VALIDASE FAA | *Aspergillus oryzae* | 10000 | — | 2 | 0/0 |
| VALIDASE FAA | *Aspergillus oryzae* | 100000 | — | 2 | 0/0 |
| AMAIZE | *Aspergillus oryzae* | 472 | — | 2 | 0.1/0.2 |
| AMAIZE | *Aspergillus oryzae* | 945 | — | 2 | 0.1/0.4 |
| AMAIZE | *Aspergillus oryzae* | 1889 | — | 4 | 0.1/0.3 |
| AMAIZE | *Aspergillus oryzae* | 10000 | — | 3 | 0/0 |
| AMAIZE | *Aspergillus oryzae* | 126349 | — | 1 | 0/0 |

The results of Table 1 clearly show that the bacterial amylases perform better than the fungal amylases which generally give rise to a very low gas production.

There also appears to be a clear dose-response effect in this model, see e.g. the STAINZYME 12L and DURAMYL 300 L DX data for gas production vs. amylase activity.

Also for the TERMAMYL SC L and NATALASE 200L amylases a clear dose-response effect is seen, but only in the lower end of the dose range—a levelling out or even a slight decline in gas production is observed for very high doses. Without wishing to be bound by any theory, this may be due to an overdosing of the formulation chemicals included in the commercial enzyme preparations.

Purified amylases having the amino acid sequences of amino acids 1-486 of SEQ ID NO: 2, 1-483 of SEQ ID NO: 4, 1-483 of SEQ ID NO: 5, 1-481 of SEQ ID NO: 6, and 1-483 of SEQ ID NO: 7 were tested as described above with same results.

Example 3

The Activity on Various Starch Substrates in vitro

Four of the amylases described in Example 2 were tested in the in vitro model of Example 1, however using a range of different starch-containing substrates instead of the TMR substrate, viz. Concentrate (standard-concentrate, commercially available from the University of Hohenheim, Institut für Tierernährung), Maize meal, Maize silage (prepared as described in Example 1), Barley meal, Rye meal, Wheat meal, Oat meal (feed grade), and Potato starch (food grade).

The results are shown in Table 2 below. In each section, the three first-mentioned amylases are bacterial amylases, whereas the last-mentioned amylase is a fungal amylase.

These amylases are described in more detail in Example 2, which also describes how the enzyme protein dose (CP, EP) and average GP was calculated.

TABLE 2

| Enzyme | mg protein (CP) | mg enzyme protein (EP) | n | Average GP (%) |
|---|---|---|---|---|
| TMR | | | | |
| STAINZYME 12L | 3108 | 1149 | 5 | 11.2 |
| TERMAMYL SC L | 1000 | 275 | 10 | 11.2 |
| DURAMYL 300L DX | 1863 | 1600 | 4 | 14.5 |
| AMAIZE | 1889 | — | 4 | 0.3 |
| Concentrate | | | | |
| STAINZYME 12L | 3108 | 1149 | 2 | 5.3 |
| TERMAMYL SC L | — | — | — | — |
| DURAMYL 300L DX | 1863 | 1600 | 2 | 7.3 |
| AMAIZE | 1889 | — | 2 | 0 |
| Maize meal | | | | |
| STAINZYME 12L | 3108 | 1149 | 5 | 35.9 |
| TERMAMYL SC L | 1000 | 275 | 2 | 73.6 |
| DURAMYL 300L DX | 1863 | 1600 | 3 | 31.8 |
| AMAIZE | 1889 | — | 3 | 0.4 |
| Maize silage | | | | |
| STAINZYME 12L | 3108 | 1149 | 2 | 28.8 |
| TERMAMYL SC L | — | — | — | — |
| DURAMYL 300L DX | 1863 | 1600 | 2 | 24.0 |
| AMAIZE | 1889 | — | 2 | 0 |
| Barley meal | | | | |
| STAINZYME 12L | 3108 | 1149 | 2 | 9.1 |
| TERMAMYL SC L | 1000 | 275 | 1 | 16.2 |
| DURAMYL 300L DX | — | — | — | — |
| AMAIZE | 1889 | — | 1 | 0 |
| Rye meal | | | | |
| STAINZYME 12L | 3108 | 1149 | 2 | 8.8 |
| TERMAMYL SC L | 1000 | 275 | 2 | 5.9 |
| DURAMYL 300L DX | — | — | — | — |
| AMAIZE | 1000 | — | 2 | 2.1 |
| Wheat meal | | | | |
| STAINZYME 12L | 3108 | 1149 | 2 | 9.5 |
| TERMAMYL SC L | 1000 | 275 | 2 | 17.7 |
| DURAMYL 300L DX | — | 1600 | — | — |
| AMAIZE | 1000 | — | 2 | 1.2 |
| Oat meal | | | | |
| STAINZYME 12L | 3108 | 1149 | 3 | 19.5 |
| TERMAMYL SC L | 1000 | 275 | 3 | 38.0 |
| DURAMYL 300L DX | — | 1600 | — | — |
| AMAIZE | 1000 | — | 3 | 1.6 |
| Potato starch | | | | |
| STAINZYME 12L | 3108 | 1149 | 1 | 18.9 |
| TERMAMYL SC L | 1000 | 275 | 1 | 35.6 |
| DURAMYL 300L DX | — | — | — | — |
| AMAIZE | 1000 | — | 1 | 3.9 |

The results of Table 2 show that the bacterial amylases had an effect on all substrates, and the effect was most pronounced on maize silage and maize meal. The TERMAMYL SC amylase appears to be the most effective bacterial amylase on all substrates. Purified amylases having the amino acid sequences of amino acids 1-486 of SEQ ID NO: 2, 1-483 of SEQ ID NO: 4, and 1-481 of SEQ ID NO: 6 were tested as described above with the same results. The effect of the fungal amylase was generally low on all substrates.

Example 4

Starch-degradation in vitro

Using the in vitro rumen system described in Example 1, the amount of starch degraded during 4 hours of in vitro rumen incubation was determined for the bacterial amylase TERMAMYL SC L, by comparing it to control samples without exogenous amylase. The substrate was TMR and the enzyme dosed 1000 mg crude protein per kg of feed.

The HFT reactions were stopped and starch precipitated by addition of 99.9% ethanol to a final concentration of 80% ethanol. The samples were centrifuged (2500×g, 4° C., 10 in.) and the supernatants discarded. For quantification of residual starch, the samples were once again precipitated with 80% ethanol and after centrifugation; acetate buffer (pH 5) was added to the residues prior to incubation at 40° C. for 15 min. followed by addition of 200 micro-liter Termamyl 300 L DX (Novozymes A/S) and continued incubation at above 90° C. for 30 min. Subsequently, temperature was lowered to 60° C., 500 micro-liter Amyloglucosidase (320 U/ml; Megazyme International) was added, and the samples were incubated for 16 hours.

The resulting glucose was quantified using the GOPOD reagent, which is a colorimetric kit employing glucose oxidase and peroxidase available from MEGAZYME International.

As shown in Table 4, the bacterial amylase lowered residual starch compared to the control sample which had also been incubated for 4 hours. The amount of starch degraded by the amylase was 18.7 mg/tube corresponding to 30% of the starch remaining in the control sample. The purified amylase having the amino acid sequence of amino acids 1-486 of SEQ ID NO: 2 was tested as described above with the same result.

TABLE 4

| Treatment | Residual starch (mg/HFT tube) Average ± std error |
|---|---|
| Control (no exogenous amylase) | 61.2 ± 2.5 |
| Bacterial amylase (TERMAMYL SC L) | 42.5 ± 1.8 |

The above experiment was repeated however replacing the bacterial amylase with the fungal AMAIZE amylase.

As shown in Table 5, the fungal amylase was not able to reduce residual starch compared to the control sample which had also been incubated for 4 hours. This is in accordance with the very low amount of gas produced in the HFT by this amylase (see Example 2).

TABLE 5

| Treatment | Residual starch (mg/HFT tube) Average ± std error |
|---|---|
| Control (no exogenous amylase) | 77.3 ± 2.5 |
| Fungal amylase (AMAIZE) | 77.3 ± 1.3 |

Example 5

Alpha-amylase Activity

Alpha-amylase activity was measured using the AMYL-kit which is commercially available from Roche Diagnostics, Cat. No. 11876473. The substrate is 4,6-ethylidene($G_7$)-p-nitrophenyl($G_1$)-alpha,D-maltoheptaoside (ethylidene-$G_7$PN P). The alpha-amylase splits off Ethylidene-$G_n$ and the resulting $G_n$-p-nitrophenyl is then cleaved by the enzyme alpha-glucosidase (part of the kit) under formation of glucose and the yellow-coloured p-nitrophenol. The rate of formation of p-nitrophenol, which is a measure of the reaction rate and thereby of the alpha-amylase activity, is observed at 405 nm, e.g. by a Konelab 30 Analyzer (commercially available from Thermo Electron Corporation), e.g. using a measuring time of 2 min.

The reaction conditions are: Temperature 37° C., pH: 7.15, reaction time: 5 min. Calcium chloride 0.03M with Brij 0.0025% (Sigma B 4184) is preferably used as a stabilizer.

The alpha-amylase activity may be given relative to a standard, e.g. in the units of KNU(S) which are determined relative to an alpha-amylase standard of a declared KNU(S) activity.

A more detailed assay description (EB-SM-0221.02) as well as a KNU(S) TERMAMYL SC standard is available on request from Novozymes A/S, Krogshoejvej 36, DK-2880 Bagsvaerd.

Example 6

Amylase pH Profiles, with and without Bile Salts

This experiment serves to determine the pH profiles of three alpha-amylases, two bacterial amylases of the invention and a prior art fungal *Aspergillus oryzae* amylase, with and without added bile salts.

The amylases used were purified *Bacillus* amylases (TERMAMYL SC and STAINZYME), and, for comparison, a purified *Aspergillus oryzae* amylase (from FUNGAMYL). These enzyme preparations are all commercially available from Novozymes A/S, Krogshoejvej 36, DK-2880 Bagsvaerd, Denmark.

Reducing Sugar Assay

Enzyme buffer: 50 mM acetate, 50 mM imidazole, 50 mM malonic acid, 1 mM $CaCl_2$, 0.01% Triton X-100. Adjust to pH 2.0, 3.0, 4.0, 5.0, 6.0, or 7.0 with HCl/NaOH.

Substrate buffer: 1.5 mg/ml amylopectin (waxy corn, e.g. Waxy corn 04201 from Cerestar, batch WM5671), 50 mM acetate, 50 mM imidazole, 50 mM malonic acid, 1 mM $CaCl_2$. Adjust to the desired pH (as above) with HCl/NaOH. Incubate for 5 min at 100° C. The substrate buffer was made with or without 5 mM bile salts (i.e. Sodium taurocholate commercially available from e.g. LGC promochem, 500 g/mol).

The amylase activity was detected by reducing sugar assay. Briefly, 50 μl enzyme (diluted in enzyme buffer so as to fall within the linear range of the assay) was mixed with 100 μl substrate buffer in PCR-MTP (Thermo-Fast 96, ABgene, cat. no. AB-0600). The MTP's were incubated at 37° C. for 15 min, following which 75 μl stop solution (100 mM p-hydroxybenzoic acid hydrazide, 180 mM K—Na-tartrate, 2% NaOH) was added, and the plates were incubated at 95° C. for 10 min. Then 150 μl from each well was transferred to 96-well MTP, and the absorbance at 410 nm was monitored as a measure of amylase activity.

The results (average of duplicate determinations) are shown in Tables 6-9, below. Table 6 shows the activity of each enzyme at the pH indicated in the absence of bile salts. For each enzyme, the maximum activity was set to 100%. Table 7 shows the same as Table 6, but in the presence of 5 mM bile salts. Table 8 shows the activity of each enzyme per mg enzyme protein at the pH indicated in the absence of bile salts, relative to the maximum enzyme activity measured in this experiment, which was the activity of the TERMAMYL SC enzyme at pH 5.0 (100%). The activity of each enzyme has accordingly been normalized relative to this activity. The amount of enzyme protein for each enzyme was determined on the basis of the specific activity. Table 9 shows the same as Table 8, but in the presence of 5 mM bile salts. Here the activity of the TERMAMYL SC enzyme at pH 5.0 in the presence of 5 mM bile salts is the reference value (100%).

TABLE 6

Relative activity without bile salts

| Enzyme | pH | | | | | |
|---|---|---|---|---|---|---|
| | 2 | 3 | 4 | 5 | 6 | 7 |
| FUNGAMYL | 0.0 | 0.0 | 77.4 | 93.4 | 100.0 | 25.6 |
| STAINZYME | 0.3 | 0.8 | 2.8 | 22.2 | 79.7 | 100.0 |
| TERMAMYL SC | 0.1 | 1.8 | 29.4 | 100.0 | 86.0 | 71.1 |

TABLE 7

Relative activity with bile salts

| Enzyme | pH | | | | | |
|---|---|---|---|---|---|---|
| | 2 | 3 | 4 | 5 | 6 | 7 |
| FUNGAMYL | 0.0 | 0.0 | 53.5 | 71.8 | 68.6 | 16.1 |
| STAINZYME | 0.0 | 0.0 | 0.8 | 2.5 | 61.4 | 78.1 |
| TERMAMYL SC | 0.0 | 0.0 | 10.4* | 76.0 | 68.6 | 59.7 |

*One measurement discarded for being clearly erroneous

TABLE 8

Normalized absolute activities relative to TERMAMYL SC without bile salts

| Enzyme | pH | | | | | |
|---|---|---|---|---|---|---|
| | 2 | 3 | 4 | 5 | 6 | 7 |
| FUNGAMYL | 0.0 | 0.0 | 10.9 | 13.2 | 14.1 | 3.6 |
| STAINZYME | 0.1 | 0.4 | 1.4 | 10.7 | 38.3 | 48.0 |
| TERMAMYL SC | 0.1 | 1.8 | 29.4 | 100.0 | 86.0 | 71.1 |

TABLE 9

Normalized absolute activities relative to TERMAMYL SC, with bile salts

| Enzyme | pH | | | | | |
|---|---|---|---|---|---|---|
| | 2 | 3 | 4 | 5 | 6 | 7 |
| FUNGAMYL | 0.0 | 0.0 | 9.9 | 13.3 | 12.7 | 3.0 |
| STAINZYME | 0.0 | 0.0 | 0.5 | 1.6 | 38.8 | 49.3 |
| TERMAMYL SC | 0.0 | 0.0 | 13.7 | 100.0 | 90.2 | 78.6 |

These results show that although bile salts seem to slightly reduce the amylase activity, the activity in the presence of 5 mM bile salts is still satisfactory. The results also show that bile salts do not lead to a shift of the pH optimum.

The results furthermore show that each of the *Bacillus* amylases of the invention all have more than 50% relative activity at pH 7, which is not the case for the comparative fungal amylase.

Finally, Tables 8 and 9 demonstrate that, at least under these conditions, the amylase from TERMAMYL SC has a significantly higher activity per mg enzyme than the other two amylases tested.

Example 7

In vivo Trial in Dairy Cows—Milk Yield

An in vivo trial was carried out with 28 dairy cows (Holstein) housed in barns with free stalls equipped with Calan gates (American Calan, Northwood, N.H.) for the measurement of individual feed intake. Cows were allowed to adjust to the gates for a three week period. Cows were then divided in blocks based on pre-trial milk production and randomly assigned to one of four treatments. The study was conducted as a 4×4 Latin square design. The four treatments were tested in four 21-days periods and data were collected for the last 7 days in each period. The bacterial TERMAMYL SC amylase (commercially available from Novozymes A/S, Krogshoejvej 36, DK-2880 Bagsvaerd, Denmark) was tested in two dosages (low=6 mg enzyme protein (EP) per kg Total Mixed Ration (TMR) dry matter (DM); high=30 mg EP/kg TMR dry matter) and compared to a control without exogenous amylase, and to the product AMAIZE (AllTech Inc., Nicholasville, Ky., US), which contains a fungal amylase. The AMAIZE dosage (240 DU/kg TMR dry matter) was based on a published trial (Tricarico et al, Animal Science 2005, 81: 365-374) showing that this was the most effective dosage out of three tested (240, 480 and 720 DU/kg TMR dry matter). The diet consisted of a TMR containing 50% concentrate, 37% corn silage, 7% alfalfa haylage, and 6% alfalfa hay. The concentrate was mainly composed of corn meal, wheat middlings, distiller's dried grain with solubles, and soy bean meal (SBM). Cows were fed the TMR ad libitum once daily, and individual feed refusals were measured daily.

Cows were milked twice daily, and milk production was recorded automatically via computer. Milk samples were taken twice daily on days 19 and 21 of each period. Milk samples were analyzed for protein and milk fat by near infrared analyses (Dairy One Laboratories, University Park, Pa., US). Fat corrected milk (FCM) was calculated as follows: FCM 3.5%=[(0.434×kg milk yield)+(16.216×kg of milk fat)]. As an example, for a Jersey cow with 30 kg milk yield and 5% fat/kg, the FCM 3.5% is (0.434×30)+(16.216×1.5)=37.34. All data were analyzed using the MIXED procedure of SAS (1999) with significance declared at $P<0.05$. Differences among treatments were determined by least squares means.

The results in the form of the average values of the different parameters measured are shown in Table 10, and the standard error of mean (SEM) values are also indicated.

TABLE 10

| Performance parameters | Control | Bacterial amylase | | Fungal amylase | SEM |
|---|---|---|---|---|---|
| | | Low dose | High dose | | |
| Dry Matter Intake (DMI) (kg/day) | 27.0[b] | 28.1[a,b] | 29.0[a] | 28.5[a] | 0.45 |
| Milk (kg/day) | 43.2[b] | 47.1[a] | 44.2[b] | 45.2[ab] | 0.74 |
| Milk/DMI (kg milk/kg DMI) | 1.60 | 1.68 | 1.52 | 1.59 | — |
| Milk fat (%) | 2.98 | 2.99 | 3.09 | 3.08 | 0.07 |
| Milk fat (kg/day) | 1.28[b] | 1.39[a] | 1.35[ab] | 1.40[a] | 0.04 |
| Milk protein (%) | 2.88 | 2.89 | 2.88 | 2.90 | 0.02 |
| Milk protein (kg/day) | 1.24[c] | 1.36[a] | 1.27[bc] | 1.30[ab] | 0.02 |
| 3.5% fat corrected milk (kg/day) | 39.4[b] | 43.0[a] | 41.0[ab] | 42.3[a] | 0.78 |
| FCM/DMI (kg milk/kg DMI) | 1.47[ab] | 1.55[a] | 1.43[b] | 1.49[ab] | 0.03 |

Means in rows with different superscripts are statistically different ($p < 0.05$)

As shown in Table 10, the bacterial amylase in the low dose significantly improved milk yield (kg/day) as well as FCM/DMI, contrary to the fungal amylase in its reported optimum dose. Milk fat (kg/day), milk protein (kg/day), as well as 3.5% fat corrected milk (FCM kg/day) were significantly improved by the bacterial amylase in the low dose as well as by the fungal amylase.

Example 8

In vivo Trial in Dairy Cows—Feed Apparent Digestibility

At the conclusion of period 4 in the in vivo trial described in example 7, the six highest producing cows from each group were continued on their experimental diets. Average daily intake was determined using data from the last week of period 4 and cows were fed this same amount daily for 8 additional days. From days 5 through 8, fecal grab samples (~300 g) were collected via rectal palpation every 8 h (the sampling point in time was increased by 1 hr each day) until a total of 12 samples were collected for each cow. During fecal collections, TMR (from each group) and orts (for each cow) were taken daily. All fecal, TMR, and orts samples (for each cow) were pooled together and dried for 48 h in a 60° C. forced air oven. Samples were ground through a 1-mm screen and analyzed for dry matter (DM), acid detergent fibre (ADF) and neutral detergent fibre (NDF) as described by Goering, H. K., Van Soest, P. J., 1970, in Forage fibre analyses (apparatus, reagents, procedures, and some applications), Agriculture Handbook No. 379, Agric. Res. Serv., USDA, Washington, D.C., USA). The samples were also analyzed for nitrogen (N) (Elementor Vario Max CN Analyzer, Elementor Americas Inc., Mt. Laurel, N.J., US), starch (Cumberland Valley Analytical Laboratory), and ash content (600° C. in a muffle furnace for 5 h). Indigestible NDF was used as a marker to calculate apparent digestibility from the total tract. Indigestible NDF was determined after 120 hr of in vitro rumen incubation (Goering and Van Soest, 1970) using a Daisy-II incubator (Ankom Technology, Macedon, N.Y., US) and rumen fluid from a cow fed the control diet. All data were analyzed using the MIXED procedure of SAS (1999) with significance declared at P<0.05. Digestibility data are presented as least-squares means in Table 11 together with standard error of means (SEM).

TABLE 11

| | Control | Bacterial amylase Low dose | Bacterial amylase High dose | Fungal amylase | SEM |
|---|---|---|---|---|---|
| Dry Matter Intake (DMI) (kg/day) | 29.59 | 26.23 | 28.33 | 27.14 | 1.30 |
| Dry matter digestibility (%) | 62.95$^{bc}$ | 68.64$^a$ | 60.52$^c$ | 65.74$^{ab}$ | 1.36 |
| Neutral-Detergent Fibre digestibility (%) | 30.02$^{bc}$ | 40.75$^a$ | 25.94$^c$ | 39.27$^{ab}$ | 3.77 |
| Organic matter digestibility (%) | 65.27$^{bc}$ | 69.94$^a$ | 61.73$^c$ | 67.37$^{ab}$ | 1.47 |
| Starch digestibility (%) | 93.34$^{ab}$ | 95.11$^a$ | 92.62$^b$ | 94.09$^{ab}$ | 0.82 |
| Crude protein digestibility (%) | 66.19$^{ab}$ | 70.00$^a$ | 61.80$^b$ | 66.73$^{ab}$ | 1.81 |

Means in rows with different superscripts are statistically different (p < 0.05)

As shown in Table 11, the bacterial amylase in the low dose significantly improved digestibility of dry matter, neutral-detergent fibre and organic matter as compared to the control sample, in contrast to the fungal amylase in its reported optimum dose. The digestibility of starch and crude protein was also numerically highest for the bacterial amylase in the low dose, but the difference was not statistically significant as compared to the control group.

Example 9

Total Tract Digestibility—and Ruminal Degradation of Feedstuffs Using the Nylon Bag Technique The enzyme used in this study was the bacterial TERMAMYL SC amylase (commercially available from Novozymes A/S, Krogshoejvej 36, DK-2880 Bagsvaerd, Denmark).

The ruminal disappearance of 8 different feedstuffs (corn grain, barley (coarse barley meal), brewer's grain, dried sugar beet pulp, corn silage, grass silage, hay and total mixed ration (TMR)) were determined by the nylon bag method (Flachowsky, G., M. Schneider, W. I. Ochrimenko, G. H. Richter, and H.-J. Löhnert, Methodische Hinweise zur Anwendung der Nylonbeutel-Technik beim Wiederkäuer. Schriftenreihe der Lehrgangseinrichtung für Fütterungsberatung Jena-Jemderoda 1988, 11: 20-26; Kurtz, H., and F. J. Schwarz, In situ—Abbaubarkeit von Restpflanzen verschiedener Maishybriden im Reifeverlauf. Übers. Tierernähg. 2005, 33: 111-120; Madsen, J., and T. Hvelplund, Prediction of in situ protein degradability in the rumen. Results of a European ring test. Acta Agric. Scand., 1994, Suppl. 25: 103-124). The brewer's grain was freeze-dried from fresh German brewer's grain from beer production based on barley. The same TMR was used as the one described below.

The feedstuffs were milled to simulate a cow's chewing and increase sample homogeneity. The corn grain, barley and sugar beet pulp samples were milled using a 3 mm screen. The hay, TMR and silage samples were first cut into smaller pieces, and then freeze-dried, except for the hay, before milling (5 mm screen). Similarly, the brewer's grain were freeze-dried and milled in this way (5 mm screen).

The study basically consisted of two treatments, namely the addition of 50 mg enzyme protein (EP) per kg dry matter (DM), and a control without enzyme. Each treatment was however two-fold, viz. in nylon bags and in the daily ration.

The enzyme was dissolved in distilled water (total volume 100 ml/kg DM) and sprayed onto the daily ration (TMR consisting of 44% corn silage, 18% grass silage, 9% hay and 29% corn based concentrate), as well as onto the feedstuff to be tested in each of the 8 nylon bag series. The same amount of distilled water was sprayed onto the control feed, and onto the control nylon bags. Enzyme/water was added to the daily ration each day, whereas enzyme/water was added to the feedstuffs in the nylon bags before the trial and deep frozen (−20° C.) until usage.

These diets (i.e. the daily ration as well as the nylon bags) were allocated to three non lactating cows (German Holstein), each fitted with a rumen canula in the dorsal rumen, in two experimental series with 3 cows per treatment, resulting in a non complete 3×3 Latin square design. The experimental group received an enzyme containing daily ration as well as enzyme-containing nylon bags, the control group received daily rations and nylon bags without enzyme addition. As regards the nylon bags, duplicate bags per incubation time containing 5 g of the different feedstuffs were placed into the rumen of three cows per treatment and the disappearance of DM was followed for up to 72 hours.

The cows were kept in an air conditioned tied-up barn (20° C.) on rubber mats with individual feeding and free access to water. The experiment lasted for 2 periods of 25 days each (in total 50 days); in each period the first 14 days were used for adaptation and the following 11 days for sampling using the nylon bags. Each cow was fed 5.5 kg (DM) TMR per day at 7:00 h and 16:00 h and 0.5 kg (DM) hay two hours after the morning feeding. In addition 100 g/d of a mineral premix was administered. From days 22 through 25, fecal grab samples (~200 g) were collected via rectal palpation at 8:30 h from each cow. $TiO_2$ was used as a marker to calculate apparent digestibility from the total tract. As an example, if you used 1% $TiO_2$ in the feed with a 10 kg feed DM intake and find 4% $TiO_2$ in the faeces, this corresponds to a faeces amount of 2.5 kg DM (as per a $TiO_2$ mass balance, in =out), in other words a crude digestibility of the feed of 75% (7.5 kg out of 10).

The results are shown in Tables 12-15 below, showing DM-disappearance (%) of corn grain, barley, corn silage, and TMR, respectively, from the nylon bag after incubation times up to 8 hours. As is usual in the art, DM was determined by drying at 105° C. until no further weight loss, normally for 24 hours. Table 16 shows the effect of amylase treatment on the in vivo nutrient apparent digestibility (% of dry matter).

TABLE 12

(Corn Grain)

| Incubation time | Control | Amylase |
|---|---|---|
| 0 | 18.0 | 18.0 |
| 2 | 25.2[b] | 33.9[a] |
| 4 | 28.4[b] | 35.9[a] |
| 8 | 32.7[b] | 43.5[a] |

Means in rows with different superscripts are statistically different (p < 0.05)

TABLE 13

(Barley)

| Incubation time | Control | Amylase |
|---|---|---|
| 0 | 23.0 | 23.0 |
| 2 | 58.8 | 64.9 |
| 4 | 70.6 | 75.1 |
| 8 | 79.9 | 81.5 |

TABLE 14

(Corn Silage)

| Incubation time | Control | Amylase |
|---|---|---|
| 0 | 51.9 | 51.9 |
| 2 | 49.3 | 50.9 |
| 4 | 50.3 | 52.0 |
| 8 | 54.3 | 54.8 |

TABLE 15

(TMR)

| Incubation time | Control | Amylase |
|---|---|---|
| 0 | 51.3 | 51.3 |
| 2 | 52.6 | 54.1 |
| 4 | 54.5 | 56.3 |
| 8 | 61.1 | 58.4 |

As is apparent from Tables 12-15, the supplementation of amylase improved the DM disappearance during incubation of the feedstuffs that contained higher amounts of starch: Significantly (p<0.05) for the corn grain (starch content of 71.9%), numerically for barley (starch content 57.6%) and corn silage (starch content of 33.1%) over the first 8 h of incubation, and numerically for the TMR (starch content of 33.0%) over the first 4 h of incubation.

As may have been expected there were no effects of the amylase on the four feedstuffs that contain no or negligible amounts of starch, i.e. grass silage, hay, sugar beet pulp and brewer's grain (data not shown).

TABLE 16

|  | Control | Amylase |
|---|---|---|
| Crude fibre | 62.3 | 64.3 |
| Crude protein | 63.1 | 64.0 |
| Organic matter | 70.1 | 71.9 |
| Crude fat | 59.0 | 62.1 |

As is apparent from Table 16, the amylase numerically increased the total tract (from mouth to faeces) apparent digestibility of crude fibre, crude protein, organic matter and crude fat in TMR, but the differences were not statistically significant. Without wishing to be bound by any theory, this may be due to one or more of the following mechanisms: The amylase affects the microflora in the rumen which can then affect the degradation of these other (non-starch) ingredients; the amylase may provide energy for growth of the microflora so that the number of microorganisms increase, and thereby the degradation of the other ingredients; removal of starch may give easier access to the other ingredients (cage effect).

The data were analyzed using the MIXED procedure of SAS (1999) with significance declared at P<0.05. Differences among treatments were determined by least squares means.

Example 10

In vivo Trial in Dairy Cows—Bacterial Amylase and Cellulase

Two groups (2×220) of dairy cows (German Holstein) were included in a 9 months feeding trial in order to test the effect of adding to the feed a combination of a bacterial amylase and cellulase.

The enzymes used were the bacterial TERMAMYL SC amylase and the CELLUCLAST cellulase, both commercially available from Novozymes A/S, Krogshoejvej 36, DK-2880 Bagsvaerd, Denmark. The CELLUCLAST cellulase is derived from *Trichoderma* reseei.

The cows were housed in a cubicle barn with slotted floors. The experimental period included three weeks before and 20 weeks after parturition. Cows were fed (eight times a day) a Total Mixed Ration (TMR) that was either not supplemented with enzyme (control) or supplemented with the amylase (1.6 ml/kg TMR, corresponding to 25 mg enzyme protein (EP)/kg TMR dry matter (DM)) and the cellulase (1.4 ml/kg TMR). The enzymes were sprayed onto the TMR immediately before feeding. The main components of the TMR were grass silage, corn silage and concentrate (mixed on the farm), and the dry matter content was approximately 50%. Animals were divided in two groups, control and treatment. We tried to compose the two groups similarly by assigning to each group individual cows of similar expected performance. This was done according to the following principle: Primiparous after predicted milk yield of father (which belongs to the normal breeding program for cows), and multiparous after lactation number and previous lactation.

The cows were milked 3 times daily in a rotary milking parlour. The individual milk yield and composition as well as the thickness of the back fat were assessed regularly during the trial.

The effect of the enzyme treatment on the milk yield is shown in FIG. 1 as the difference in milk yield (kg/d) between the treated group and the control group as a function of days after parturition.

The use of amylase and cellulase in combination resulted in increased milk yield (without any changes in milk composition; data not shown) in the early lactation phase. The differences were significant from day 1 through 14, and the effect was no longer evident in late lactation.

Figure 2:
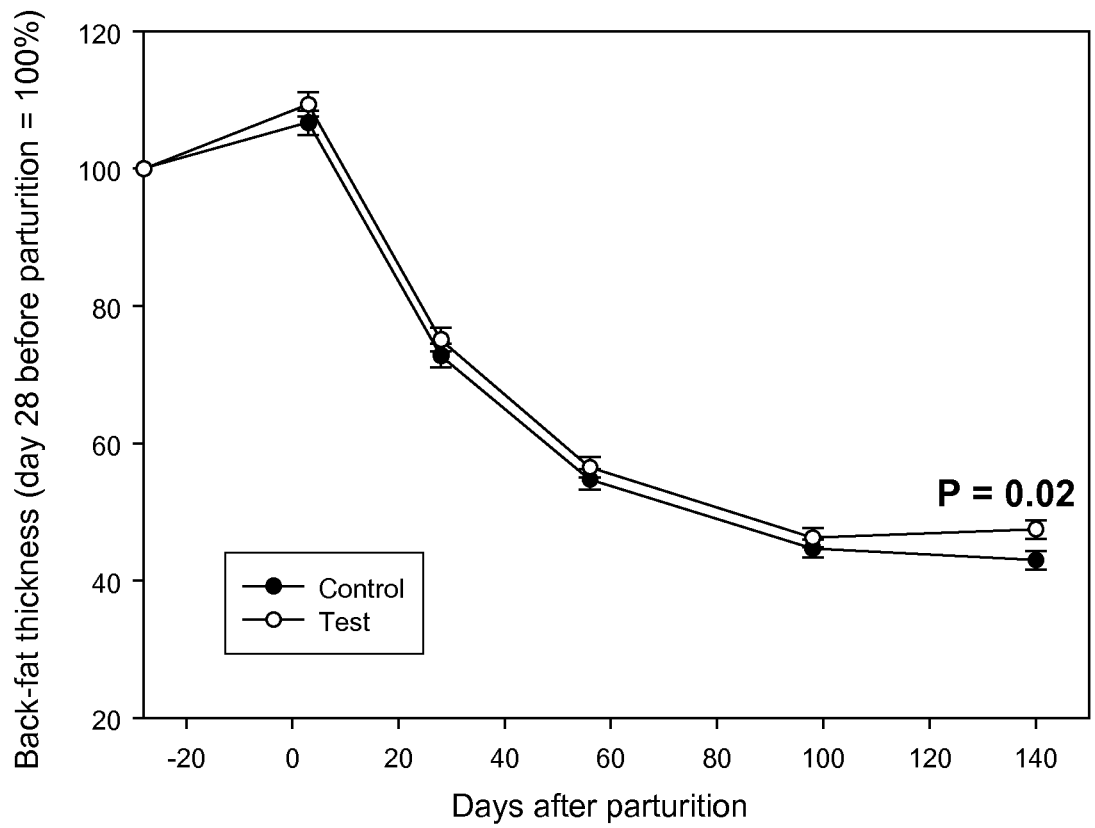

The back-fat thicknesses of the two groups are shown in FIG. 2 as a function of days after parturition (normalised so that the level of back-fat thickness on day 28 before parturition is set to 100%). The enzyme treated group (○) had higher levels of back-fat thickness during the trial as compared to the control (●), and the effect was statistically significant on day 140 after parturition (p=0.02).

Example 11

In vivo Trial in Dairy Cows: Milk Yield, Digestibility, Nylon Bag Experiments

The purified bacterial amylase having the amino acid sequence of amino acids 1-486 of SEQ ID NO: 2 was tested in vivo in dairy cows as described in Examples 7-10. The same results were obtained.

Example 12

Feed Additive Compositions

The TERMAMYL SC amylase is mixed with a vitamin and mineral premix (also called mineral feed) composed as follows per kg: 14% Calcium, 9.5% Sodium, 6% Phosphorus, 5% Magnesium, 800 000 IU Vitamin A, 120 000 IU Vitamin D3, 3000 mg Vitamin E, 130 mg Vitamin B1, 78 mg Vitamin B2, 70 mg Vitamin B6, 525 μg Vitamin B12, 21 mg Folic acid, 260 mg Ca D-Pantothenate, 2500 mg Niacin, 130 000 μg Biotin, 8500 mg Zinc, 4000 mg Manganese, 1200 mg Copper, 100 mg Iodine, 21 mg Cobalt, 50 mg Selenium. The percentages indicated are w/w. The TERMAMYL SC amylase is included in an amount corresponding to 1.8 g enzyme protein/kg of the premix. The premix is fed at a rate of 100 g per animal and day. The assumed feed consumption per day is 30 kg (DM).

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

Various references are cited herein, the disclosures of which are incorporated by reference in their entireties.

The invention claimed is:

1. A method for increasing milk yield or improving organic matter digestibility in a dairy cow or beef cattle, comprising feeding the dairy cow or beef cattle with a feed which comprises an alpha-amylase, wherein
the alpha-amylase is selected from the group consisting of the sequence of amino acids 1-481 of SEQ ID NO: 2, the sequence of amino acids 1-484 of SEQ ID NO: 2, the sequence of amino acids 1-486 of SEQ ID NO: 2, and the sequence of amino acids 1-513 of SEQ ID NO: 2; and
the alpha-amylase is added in an amount to increase milk yield or to improve organic matter digestibility in a dairy cow or beef cattle, wherein the amount is in the range of 3-20 mg enzyme protein/kg diet dry matter.

2. The method of claim 1, wherein the alpha-amylase has the sequence of 1-481 of SEQ ID NO: 2.

3. The method of claim 1, wherein the alpha-amylase has the sequence of 1-484 of SEQ ID NO: 2.

4. The method of claim 1, wherein the alpha-amylase has the sequence of 1-486 of SEQ ID NO: 2.

5. The method of claim 1, wherein the alpha-amylase has the sequence of 1-513 of SEQ ID NO: 2.

6. The method of claim 1, wherein the feed further comprises a cellulase.

7. The method of claim 1, wherein the feed further comprises a vitamin and/or mineral.

8. The method of claim 1, wherein the feed further comprises at least one additional ingredient selected from the group consisting of hay, forage, and roughage.

9. The method of claim 1, wherein the feed further comprises maize and/or sorghum.

10. The method of claim 1, wherein the alpha-amylase is added in an amount in the range of 4-15 mg enzyme protein/kg diet dry matter.

* * * * *

SEQUENCE LISTING

```
<160> NUMBER OF SEQ ID NOS: 9

<210> SEQ ID NO 1
<211> LENGTH: 1620
<212> TYPE: DNA
<213> ORGANISM: Artificial Sequence
<220> FEATURE:
<223> OTHER INFORMATION: Variant of DNA from Bacillus stearothermophilus
<220> FEATURE:
<221> NAME/KEY: sig_peptide
<222> LOCATION: (1)..(81)
<220> FEATURE:
<221> NAME/KEY: CDS
<222> LOCATION: (1)..(1620)
<220> FEATURE:
<221> NAME/KEY: mat_peptide
<222> LOCATION: (82)..(1620)

<400> SEQUENCE: 1 atg aaa caa caa aaa cgg ctt tac gcc cga ttg ctg acg ctg tta ttt        48
Met Lys Gln Gln Lys Arg Leu Tyr Ala Arg Leu Leu Thr Leu Leu Phe
        -25                 -20                 -15 gcg ctc atc ttc ttg ctg cct cat tct gca gcc gcg gca ccg ttt aac        96
Ala Leu Ile Phe Leu Leu Pro His Ser Ala Ala Ala Ala Pro Phe Asn
    -10                  -5                  -1   1               5 ggc acc atg atg cag tat ttt gaa tgg tac ttg ccg gat gat ggc acg       144
Gly Thr Met Met Gln Tyr Phe Glu Trp Tyr Leu Pro Asp Asp Gly Thr
                 10                  15                  20 tta tgg acc aaa gtg gcc aat gaa gcc aac aac tta tcc agc ctt ggc       192
Leu Trp Thr Lys Val Ala Asn Glu Ala Asn Asn Leu Ser Ser Leu Gly
             25                  30                  35
```

-continued

| | | |
|---|---|---|
| atc acc gct ctt tgg ctg ccg ccc gct tac aaa gga aca agc cgc agc<br>Ile Thr Ala Leu Trp Leu Pro Pro Ala Tyr Lys Gly Thr Ser Arg Ser<br>        40                        45                        50 | 240 | |
| gac gta ggg tac gga gta tac gac ttg tat gac ctc ggc gaa ttc aat<br>Asp Val Gly Tyr Gly Val Tyr Asp Leu Tyr Asp Leu Gly Glu Phe Asn<br>    55                        60                      65 | 288 | |
| caa aaa ggg acc gtc cgc aca aaa tac gga aca aaa gct caa tat ctt<br>Gln Lys Gly Thr Val Arg Thr Lys Tyr Gly Thr Lys Ala Gln Tyr Leu<br>70                  75                        80                      85 | 336 | |
| caa gcc att caa gcc gcc cac gcc gct gga atg caa gtg tac gcc gat<br>Gln Ala Ile Gln Ala Ala His Ala Ala Gly Met Gln Val Tyr Ala Asp<br>                90                        95                        100 | 384 | |
| gtc gtg ttc gac cat aaa ggc ggc gct gac ggc acg gaa tgg gtg gac<br>Val Val Phe Asp His Lys Gly Gly Ala Asp Gly Thr Glu Trp Val Asp<br>            105                      110                      115 | 432 | |
| gcc gtc gaa gtc aat ccg tcc gac cgc aac caa gaa atc tcg ggc acc<br>Ala Val Glu Val Asn Pro Ser Asp Arg Asn Gln Glu Ile Ser Gly Thr<br>120                  125                      130 | 480 | |
| tat caa atc caa gca tgg acg aaa ttt gat ttt ccc ggg cgg ggc aac<br>Tyr Gln Ile Gln Ala Trp Thr Lys Phe Asp Phe Pro Gly Arg Gly Asn<br>        135                      140                      145 | 528 | |
| acc tac tcc agc ttt aag tgg cgc tgg tac cat ttt gac ggc gtt gat<br>Thr Tyr Ser Ser Phe Lys Trp Arg Trp Tyr His Phe Asp Gly Val Asp<br>150                  155                      160                      165 | 576 | |
| tgg gac gaa agc cga aaa ttg agc cgc att tac aaa ttc cgt ggc aag<br>Trp Asp Glu Ser Arg Lys Leu Ser Arg Ile Tyr Lys Phe Arg Gly Lys<br>                170                      175                      180 | 624 | |
| gct tgg gat tgg gaa gta gac acg gaa ttc gga aac tat gac tac tta<br>Ala Trp Asp Trp Glu Val Asp Thr Glu Phe Gly Asn Tyr Asp Tyr Leu<br>            185                      190                      195 | 672 | |
| atg tat gcc gac ctt gat atg gat cat ccc gaa gtc gtg acc gag ctg<br>Met Tyr Ala Asp Leu Asp Met Asp His Pro Glu Val Val Thr Glu Leu<br>                200                      205                      210 | 720 | |
| aaa aac tgg ggg aaa tgg tat gtc aac aca acg aac att gat ggg ttc<br>Lys Asn Trp Gly Lys Trp Tyr Val Asn Thr Thr Asn Ile Asp Gly Phe<br>215                  220                      225 | 768 | |
| cgg ctt gat gcc gtc aag cat att aag ttc agt ttt ttt cct gat tgg<br>Arg Leu Asp Ala Val Lys His Ile Lys Phe Ser Phe Phe Pro Asp Trp<br>230                  235                      240                      245 | 816 | |
| ttg tcg tat gtg cgt tct cag act ggc aag ccg cta ttt acc gtc ggg<br>Leu Ser Tyr Val Arg Ser Gln Thr Gly Lys Pro Leu Phe Thr Val Gly<br>            250                      255                      260 | 864 | |
| gaa tat tgg agc tat gac atc aac aag ttg cac aat tac att acg aaa<br>Glu Tyr Trp Ser Tyr Asp Ile Asn Lys Leu His Asn Tyr Ile Thr Lys<br>                265                      270                      275 | 912 | |
| aca gac gga acg atg tct ttg ttt gat gcc ccg tta cac aac aaa ttt<br>Thr Asp Gly Thr Met Ser Leu Phe Asp Ala Pro Leu His Asn Lys Phe<br>            280                      285                      290 | 960 | |
| tat acc gct tcc aaa tca ggg ggc gca ttt gat atg cgc acg tta atg<br>Tyr Thr Ala Ser Lys Ser Gly Gly Ala Phe Asp Met Arg Thr Leu Met<br>295                  300                      305 | 1008 | |
| acc aat act ctc atg aaa gat caa ccg aca ttg gcc gtc acc ttc gtt<br>Thr Asn Thr Leu Met Lys Asp Gln Pro Thr Leu Ala Val Thr Phe Val<br>310                  315                      320                      325 | 1056 | |
| gat aat cat gac acc gaa ccc ggc caa gcg ctg caa tca tgg gtc gac<br>Asp Asn His Asp Thr Glu Pro Gly Gln Ala Leu Gln Ser Trp Val Asp<br>                330                      335                      340 | 1104 | |
| cca tgg ttc aaa ccg ttg gct tac gcc ttt att cta act cgg cag gaa<br>Pro Trp Phe Lys Pro Leu Ala Tyr Ala Phe Ile Leu Thr Arg Gln Glu<br>            345                      350                      355 | 1152 | |

```
gga tac ccg tgc gtc ttt tat ggt gac tat tat ggc att cca caa tat      1200
Gly Tyr Pro Cys Val Phe Tyr Gly Asp Tyr Tyr Gly Ile Pro Gln Tyr
        360                 365                 370 aac att cct tcg ctg aaa agc aaa atc gat ccg ctc ctc atc gcg cgc      1248
Asn Ile Pro Ser Leu Lys Ser Lys Ile Asp Pro Leu Leu Ile Ala Arg
375                 380                 385 agg gat tat gct tac gga acg caa cat gat tat ctt gat cac tcc gac      1296
Arg Asp Tyr Ala Tyr Gly Thr Gln His Asp Tyr Leu Asp His Ser Asp
390                 395                 400                 405 atc atc ggg tgg aca agg gaa ggg ggc act gaa aaa cca gga tcc gga      1344
Ile Ile Gly Trp Thr Arg Glu Gly Gly Thr Glu Lys Pro Gly Ser Gly
        410                 415                 420 ctg gcc gca ctg atc acc gat ggg ccg gga gga agc aaa tgg atg tac      1392
Leu Ala Ala Leu Ile Thr Asp Gly Pro Gly Gly Ser Lys Trp Met Tyr
        425                 430                 435 gtt ggc aaa caa cac gct gga aaa gtg ttc tat gac ctt acc ggc aac      1440
Val Gly Lys Gln His Ala Gly Lys Val Phe Tyr Asp Leu Thr Gly Asn
        440                 445                 450 cgg agt gac acc gtc acc atc aac agt gat gga tgg ggg gaa ttc aaa      1488
Arg Ser Asp Thr Val Thr Ile Asn Ser Asp Gly Trp Gly Glu Phe Lys
455                 460                 465 gtc aat ggc ggt tcg gtt tcg gtt tgg gtt cct aga aaa acg acc gtt      1536
Val Asn Gly Gly Ser Val Ser Val Trp Val Pro Arg Lys Thr Thr Val
470                 475                 480                 485 tct acc atc gct cgg ccg atc aca acc cga ccg tgg act ggt gaa ttc      1584
Ser Thr Ile Ala Arg Pro Ile Thr Thr Arg Pro Trp Thr Gly Glu Phe
        490                 495                 500 gtc cgt tgg acc gaa cca cgg ttg gtg gca tgg cct                      1620
Val Arg Trp Thr Glu Pro Arg Leu Val Ala Trp Pro
        505                 510

<210> SEQ ID NO 2
<211> LENGTH: 540
<212> TYPE: PRT
<213> ORGANISM: Artificial Sequence
<220> FEATURE:
<223> OTHER INFORMATION: Synthetic Construct

<400> SEQUENCE: 2

Met Lys Gln Gln Lys Arg Leu Tyr Ala Arg Leu Leu Thr Leu Leu Phe
        -25                 -20                 -15

Ala Leu Ile Phe Leu Leu Pro His Ser Ala Ala Ala Pro Phe Asn
    -10                  -5              -1   1              5

Gly Thr Met Met Gln Tyr Phe Glu Trp Tyr Leu Pro Asp Asp Gly Thr
                10                  15                  20

Leu Trp Thr Lys Val Ala Asn Glu Ala Asn Asn Leu Ser Ser Leu Gly
            25                  30                  35

Ile Thr Ala Leu Trp Leu Pro Pro Ala Tyr Lys Gly Thr Ser Arg Ser
        40                  45                  50

Asp Val Gly Tyr Gly Val Tyr Asp Leu Tyr Asp Leu Gly Glu Phe Asn
55                  60                  65

Gln Lys Gly Thr Val Arg Thr Lys Tyr Gly Thr Lys Ala Gln Tyr Leu
70                  75                  80                  85

Gln Ala Ile Gln Ala Ala His Ala Gly Met Gln Val Tyr Ala Asp
            90                  95                  100

Val Val Phe Asp His Lys Gly Gly Ala Asp Gly Thr Glu Trp Val Asp
        105                 110                 115

Ala Val Glu Val Asn Pro Ser Asp Arg Asn Gln Glu Ile Ser Gly Thr
```

120                 125                 130
Tyr Gln Ile Gln Ala Trp Thr Lys Phe Asp Phe Pro Gly Arg Gly Asn
135                 140                 145

Thr Tyr Ser Ser Phe Lys Trp Arg Trp Tyr His Phe Asp Gly Val Asp
150                 155                 160                 165

Trp Asp Glu Ser Arg Lys Leu Ser Arg Ile Tyr Lys Phe Arg Gly Lys
                170                 175                 180

Ala Trp Asp Trp Glu Val Asp Thr Glu Phe Gly Asn Tyr Asp Tyr Leu
            185                 190                 195

Met Tyr Ala Asp Leu Asp Met Asp His Pro Glu Val Val Thr Glu Leu
        200                 205                 210

Lys Asn Trp Gly Lys Trp Tyr Val Asn Thr Thr Asn Ile Asp Gly Phe
    215                 220                 225

Arg Leu Asp Ala Val Lys His Ile Lys Phe Ser Phe Pro Asp Trp
230                 235                 240                 245

Leu Ser Tyr Val Arg Ser Gln Thr Gly Lys Pro Leu Phe Thr Val Gly
                250                 255                 260

Glu Tyr Trp Ser Tyr Asp Ile Asn Lys Leu His Asn Tyr Ile Thr Lys
            265                 270                 275

Thr Asp Gly Thr Met Ser Leu Phe Asp Ala Pro Leu His Asn Lys Phe
        280                 285                 290

Tyr Thr Ala Ser Lys Ser Gly Gly Ala Phe Asp Met Arg Thr Leu Met
    295                 300                 305

Thr Asn Thr Leu Met Lys Asp Gln Pro Thr Leu Ala Val Thr Phe Val
310                 315                 320                 325

Asp Asn His Asp Thr Glu Pro Gly Gln Ala Leu Gln Ser Trp Val Asp
                330                 335                 340

Pro Trp Phe Lys Pro Leu Ala Tyr Ala Phe Ile Leu Thr Arg Gln Glu
            345                 350                 355

Gly Tyr Pro Cys Val Phe Tyr Gly Asp Tyr Tyr Gly Ile Pro Gln Tyr
        360                 365                 370

Asn Ile Pro Ser Leu Lys Ser Lys Ile Asp Pro Leu Leu Ile Ala Arg
    375                 380                 385

Arg Asp Tyr Ala Tyr Gly Thr Gln His Asp Tyr Leu Asp His Ser Asp
390                 395                 400                 405

Ile Ile Gly Trp Thr Arg Glu Gly Gly Thr Glu Lys Pro Gly Ser Gly
                410                 415                 420

Leu Ala Ala Leu Ile Thr Asp Gly Pro Gly Gly Ser Lys Trp Met Tyr
            425                 430                 435

Val Gly Lys Gln His Ala Gly Lys Val Phe Tyr Asp Leu Thr Gly Asn
        440                 445                 450

Arg Ser Asp Thr Val Thr Ile Asn Ser Asp Gly Trp Gly Glu Phe Lys
    455                 460                 465

Val Asn Gly Gly Ser Val Ser Val Trp Val Pro Arg Lys Thr Thr Val
470                 475                 480                 485

Ser Thr Ile Ala Arg Pro Ile Thr Thr Arg Pro Trp Thr Gly Glu Phe
                490                 495                 500

Val Arg Trp Thr Glu Pro Arg Leu Val Ala Trp Pro
            505                 510

<210> SEQ ID NO 3
<211> LENGTH: 1449
<212> TYPE: DNA
<213> ORGANISM: Artificial Sequence

```
<220> FEATURE:
<223> OTHER INFORMATION: Variant of DNA from Bacillus sp.
<220> FEATURE:
<221> NAME/KEY: CDS
<222> LOCATION: (1)..(1449)
<220> FEATURE:
<221> NAME/KEY: mat_peptide
<222> LOCATION: (1)..(1449)

<400> SEQUENCE: 3 cac cat aat ggt acg aac ggc aca atg atg cag tac ttt gaa tgg tat      48
His His Asn Gly Thr Asn Gly Thr Met Met Gln Tyr Phe Glu Trp Tyr
1               5                   10                  15 cta cca aat gac gga aac cat tgg aat aga tta agg tct gat gca agt      96
Leu Pro Asn Asp Gly Asn His Trp Asn Arg Leu Arg Ser Asp Ala Ser
                20                  25                  30 aac cta aaa gat aaa ggg atc tca gcg gtt tgg att cct cct gca tgg     144
Asn Leu Lys Asp Lys Gly Ile Ser Ala Val Trp Ile Pro Pro Ala Trp
            35                  40                  45 aag ggt gcc tct caa aat gat gtg ggg tat ggt gct tat gat ctg tat     192
Lys Gly Ala Ser Gln Asn Asp Val Gly Tyr Gly Ala Tyr Asp Leu Tyr
        50                  55                  60 gat tta gga gaa ttc aat caa aaa gga acc att cgt aca aaa tat gga     240
Asp Leu Gly Glu Phe Asn Gln Lys Gly Thr Ile Arg Thr Lys Tyr Gly
65                  70                  75                  80 acg cgc aat cag tta caa gct gcg gtt aac gcc ttg aaa agt aat gga     288
Thr Arg Asn Gln Leu Gln Ala Ala Val Asn Ala Leu Lys Ser Asn Gly
                85                  90                  95 att caa gtg tat ggc gat gtt gta atg aat cat aaa ggg gga gca gac     336
Ile Gln Val Tyr Gly Asp Val Val Met Asn His Lys Gly Gly Ala Asp
            100                 105                 110 gct acc gaa atg gtt aaa gca gtc gaa gta aac ccg aat aat aga aat     384
Ala Thr Glu Met Val Lys Ala Val Glu Val Asn Pro Asn Asn Arg Asn
        115                 120                 125 caa gaa gtg tcc ggt gaa tat aca att gag gct tgg aca aag ttt gac     432
Gln Glu Val Ser Gly Glu Tyr Thr Ile Glu Ala Trp Thr Lys Phe Asp
    130                 135                 140 ttt cca gga cga ggt aat act cat tca aac ttc aaa tgg aga tgg tat     480
Phe Pro Gly Arg Gly Asn Thr His Ser Asn Phe Lys Trp Arg Trp Tyr
145                 150                 155                 160 cac ttt gat gga gta gat tgg gat cag tca cgt aag ctg aac aat cga     528
His Phe Asp Gly Val Asp Trp Asp Gln Ser Arg Lys Leu Asn Asn Arg
                165                 170                 175 att tat aaa ttc cgc ggt aaa ggg tgg gat tgg gaa gtc gat aca gaa     576
Ile Tyr Lys Phe Arg Gly Lys Gly Trp Asp Trp Glu Val Asp Thr Glu
            180                 185                 190 ttc ggt aac tat gat tac cta atg tat gca gat att gac atg gat cac     624
Phe Gly Asn Tyr Asp Tyr Leu Met Tyr Ala Asp Ile Asp Met Asp His
        195                 200                 205 cca gag gta gtg aat gag cta aga aat tgg ggt gtt tgg tat acg aat     672
Pro Glu Val Val Asn Glu Leu Arg Asn Trp Gly Val Trp Tyr Thr Asn
    210                 215                 220 aca tta ggc ctt gat ggt ttt aga ata gat gca gta aaa cat ata aaa     720
Thr Leu Gly Leu Asp Gly Phe Arg Ile Asp Ala Val Lys His Ile Lys
225                 230                 235                 240 tac agc ttt act cgt gat tgg att aat cat gtt aga agt gca act ggc     768
Tyr Ser Phe Thr Arg Asp Trp Ile Asn His Val Arg Ser Ala Thr Gly
                245                 250                 255 aaa aat atg ttt gcg gtt gcg gaa ttt tgg aaa aat gat tta ggt gct     816
Lys Asn Met Phe Ala Val Ala Glu Phe Trp Lys Asn Asp Leu Gly Ala
            260                 265                 270
```

-continued

| | | |
|---|---|---|
| att gaa aac tat tta aac aaa aca aac tgg aac cat tca gtc ttt gat<br>Ile Glu Asn Tyr Leu Asn Lys Thr Asn Trp Asn His Ser Val Phe Asp<br>275     280     285 | | 864 |
| gtt ccg ctg cac tat aac ctc tat aat gct tca aaa agc gga ggg aat<br>Val Pro Leu His Tyr Asn Leu Tyr Asn Ala Ser Lys Ser Gly Gly Asn<br>290     295     300 | | 912 |
| tat gat atg agg caa ata ttt aat ggt aca gtc gtg caa aag cat cca<br>Tyr Asp Met Arg Gln Ile Phe Asn Gly Thr Val Val Gln Lys His Pro<br>305     310     315     320 | | 960 |
| atg cat gct gtt aca ttt gtt gat aat cat gat tcg caa cct gaa gaa<br>Met His Ala Val Thr Phe Val Asp Asn His Asp Ser Gln Pro Glu Glu<br>     325     330     335 | | 1008 |
| gct tta gag tct ttt gtt gaa gaa tgg ttc aaa cca tta gcg tat gct<br>Ala Leu Glu Ser Phe Val Glu Glu Trp Phe Lys Pro Leu Ala Tyr Ala<br>340     345     350 | | 1056 |
| ttg aca tta aca cgt gaa caa ggc tac cct tct gta ttt tat gga gat<br>Leu Thr Leu Thr Arg Glu Gln Gly Tyr Pro Ser Val Phe Tyr Gly Asp<br>355     360     365 | | 1104 |
| tat tat ggc att cca acg cat ggt gta cca gcg atg aaa tcg aaa att<br>Tyr Tyr Gly Ile Pro Thr His Gly Val Pro Ala Met Lys Ser Lys Ile<br>370     375     380 | | 1152 |
| gac ccg att cta gaa gcg cgt caa aag tat gca tat gga aga caa aat<br>Asp Pro Ile Leu Glu Ala Arg Gln Lys Tyr Ala Tyr Gly Arg Gln Asn<br>385     390     395     400 | | 1200 |
| gac tac tta gac cat cat aat atc atc ggt tgg aca cgt gaa ggg aat<br>Asp Tyr Leu Asp His His Asn Ile Ile Gly Trp Thr Arg Glu Gly Asn<br>     405     410     415 | | 1248 |
| aca gca cac ccc aac tcc ggt tta gct act atc atg tcc gat ggg gca<br>Thr Ala His Pro Asn Ser Gly Leu Ala Thr Ile Met Ser Asp Gly Ala<br>420     425     430 | | 1296 |
| gga gga aat aag tgg atg ttt gtt ggg cgt aat aaa gct ggt caa gtt<br>Gly Gly Asn Lys Trp Met Phe Val Gly Arg Asn Lys Ala Gly Gln Val<br>435     440     445 | | 1344 |
| tgg acc gat atc act gga aat aaa gcc ggt act gtt acg att aat gct<br>Trp Thr Asp Ile Thr Gly Asn Lys Ala Gly Thr Val Thr Ile Asn Ala<br>450     455     460 | | 1392 |
| gat gga tgg ggt aat ttt tct gta aat gga gga tca gtt tct att tgg<br>Asp Gly Trp Gly Asn Phe Ser Val Asn Gly Gly Ser Val Ser Ile Trp<br>465     470     475     480 | | 1440 |
| gta aac aaa<br>Val Asn Lys | | 1449 |

<210> SEQ ID NO 4
<211> LENGTH: 483
<212> TYPE: PRT
<213> ORGANISM: Artificial Sequence
<220> FEATURE:
<223> OTHER INFORMATION: Synthetic Construct

<400> SEQUENCE: 4

His His Asn Gly Thr Asn Gly Thr Met Met Gln Tyr Phe Glu Trp Tyr
1     5     10     15

Leu Pro Asn Asp Gly Asn His Trp Asn Arg Leu Arg Ser Asp Ala Ser
     20     25     30

Asn Leu Lys Asp Lys Gly Ile Ser Ala Val Trp Ile Pro Pro Ala Trp
   35     40     45

Lys Gly Ala Ser Gln Asn Asp Val Gly Tyr Gly Ala Tyr Asp Leu Tyr
 50     55     60

Asp Leu Gly Glu Phe Asn Gln Lys Gly Thr Ile Arg Thr Lys Tyr Gly
65     70     75     80

```
Thr Arg Asn Gln Leu Gln Ala Ala Val Asn Ala Leu Lys Ser Asn Gly
                85                  90                  95

Ile Gln Val Tyr Gly Asp Val Val Met Asn His Lys Gly Gly Ala Asp
            100                 105                 110

Ala Thr Glu Met Val Lys Ala Val Glu Val Asn Pro Asn Asn Arg Asn
        115                 120                 125

Gln Glu Val Ser Gly Glu Tyr Thr Ile Glu Ala Trp Thr Lys Phe Asp
    130                 135                 140

Phe Pro Gly Arg Gly Asn Thr His Ser Asn Phe Lys Trp Arg Trp Tyr
145                 150                 155                 160

His Phe Asp Gly Val Asp Trp Asp Gln Ser Arg Lys Leu Asn Asn Arg
                165                 170                 175

Ile Tyr Lys Phe Arg Gly Lys Gly Trp Asp Trp Glu Val Asp Thr Glu
            180                 185                 190

Phe Gly Asn Tyr Asp Tyr Leu Met Tyr Ala Asp Ile Asp Met Asp His
        195                 200                 205

Pro Glu Val Val Asn Glu Leu Arg Asn Trp Gly Val Trp Tyr Thr Asn
    210                 215                 220

Thr Leu Gly Leu Asp Gly Phe Arg Ile Asp Ala Val Lys His Ile Lys
225                 230                 235                 240

Tyr Ser Phe Thr Arg Asp Trp Ile Asn His Val Arg Ser Ala Thr Gly
                245                 250                 255

Lys Asn Met Phe Ala Val Ala Glu Phe Trp Lys Asn Asp Leu Gly Ala
            260                 265                 270

Ile Glu Asn Tyr Leu Asn Lys Thr Asn Trp Asn His Ser Val Phe Asp
        275                 280                 285

Val Pro Leu His Tyr Asn Leu Tyr Asn Ala Ser Lys Ser Gly Gly Asn
    290                 295                 300

Tyr Asp Met Arg Gln Ile Phe Asn Gly Thr Val Val Gln Lys His Pro
305                 310                 315                 320

Met His Ala Val Thr Phe Val Asp Asn His Asp Ser Gln Pro Glu Glu
                325                 330                 335

Ala Leu Glu Ser Phe Val Glu Glu Trp Phe Lys Pro Leu Ala Tyr Ala
            340                 345                 350

Leu Thr Leu Thr Arg Glu Gln Gly Tyr Pro Ser Val Phe Tyr Gly Asp
        355                 360                 365

Tyr Tyr Gly Ile Pro Thr His Gly Val Pro Ala Met Lys Ser Lys Ile
    370                 375                 380

Asp Pro Ile Leu Glu Ala Arg Gln Lys Tyr Ala Tyr Gly Arg Gln Asn
385                 390                 395                 400

Asp Tyr Leu Asp His His Asn Ile Ile Gly Trp Thr Arg Glu Gly Asn
                405                 410                 415

Thr Ala His Pro Asn Ser Gly Leu Ala Thr Ile Met Ser Asp Gly Ala
            420                 425                 430

Gly Gly Asn Lys Trp Met Phe Val Gly Arg Asn Lys Ala Gly Gln Val
        435                 440                 445

Trp Thr Asp Ile Thr Gly Asn Lys Ala Gly Thr Val Thr Ile Asn Ala
    450                 455                 460

Asp Gly Trp Gly Asn Phe Ser Val Asn Gly Gly Ser Val Ser Ile Trp
465                 470                 475                 480

Val Asn Lys
```

```
<210> SEQ ID NO 5
<211> LENGTH: 483
<212> TYPE: PRT
<213> ORGANISM: Artificial Sequence
<220> FEATURE:
<223> OTHER INFORMATION: Variant of enzyme from Bacillus halmapalus
<220> FEATURE:
<221> NAME/KEY: mat_peptide
<222> LOCATION: (1)..(483)

<400> SEQUENCE: 5

His His Asn Gly Thr Asn Gly Thr Met Met Gln Tyr Phe Glu Trp His
1               5                   10                  15

Leu Pro Asn Asp Gly Asn His Trp Asn Arg Leu Arg Asp Asp Ala Ser
            20                  25                  30

Asn Leu Arg Asn Arg Gly Ile Thr Ala Ile Trp Ile Pro Pro Ala Trp
        35                  40                  45

Lys Gly Thr Ser Gln Asn Asp Val Gly Tyr Gly Ala Tyr Asp Leu Tyr
    50                  55                  60

Asp Leu Gly Glu Phe Asn Gln Lys Gly Thr Val Arg Thr Lys Tyr Gly
65                  70                  75                  80

Thr Arg Ser Gln Leu Glu Ser Ala Ile His Ala Leu Lys Asn Asn Gly
                85                  90                  95

Val Gln Val Tyr Gly Asp Val Val Met Asn His Lys Gly Gly Ala Asp
            100                 105                 110

Ala Thr Glu Asn Val Leu Ala Val Glu Val Asn Pro Asn Asn Arg Asn
        115                 120                 125

Gln Glu Ile Ser Gly Asp Tyr Thr Ile Glu Ala Trp Thr Lys Phe Asp
    130                 135                 140

Phe Pro Gly Arg Gly Asn Thr Tyr Ser Asp Phe Lys Trp Arg Trp Tyr
145                 150                 155                 160

His Phe Asp Gly Val Asp Trp Asp Gln Ser Arg Gln Phe Gln Asn Arg
                165                 170                 175

Ile Tyr Lys Phe Arg Gly Lys Ala Trp Asp Trp Glu Val Asp Ser Glu
            180                 185                 190

Asn Gly Asn Tyr Asp Tyr Leu Met Tyr Ala Asp Val Asp Met Asp His
        195                 200                 205

Pro Glu Val Val Asn Glu Leu Arg Arg Trp Gly Glu Trp Tyr Thr Asn
    210                 215                 220

Thr Leu Asn Leu Asp Gly Phe Arg Ile Asp Ala Val Lys His Ile Lys
225                 230                 235                 240

Tyr Ser Phe Thr Arg Asp Trp Leu Thr His Val Arg Asn Ala Thr Gly
                245                 250                 255

Lys Glu Met Phe Ala Val Ala Glu Phe Trp Lys Asn Asp Leu Gly Ala
            260                 265                 270

Leu Glu Asn Tyr Leu Asn Lys Thr Asn Trp Asn His Ser Val Phe Asp
        275                 280                 285

Val Pro Leu His Tyr Asn Leu Tyr Asn Ala Ser Asn Ser Gly Gly Asn
    290                 295                 300

Tyr Asp Met Ala Lys Leu Leu Asn Gly Thr Val Val Gln Lys His Pro
305                 310                 315                 320

Met His Ala Val Thr Phe Val Asp Asn His Asp Ser Gln Pro Gly Glu
                325                 330                 335

Ser Leu Glu Ser Phe Val Gln Glu Trp Phe Lys Pro Leu Ala Tyr Ala
            340                 345                 350

Leu Ile Leu Thr Arg Glu Gln Gly Tyr Pro Ser Val Phe Tyr Gly Asp
```

```
                    355                 360                 365
Tyr Tyr Gly Ile Pro Thr His Ser Val Pro Ala Met Lys Ala Lys Ile
370                 375                 380

Asp Pro Ile Leu Glu Ala Arg Gln Asn Phe Ala Tyr Gly Thr Gln His
385                 390                 395                 400

Asp Tyr Phe Asp His Asn Ile Ile Gly Trp Thr Arg Glu Gly Asn
                405                 410                 415

Thr Thr His Pro Asn Ser Gly Leu Ala Thr Ile Met Ser Asp Gly Pro
                420                 425                 430

Gly Gly Glu Lys Trp Met Tyr Val Gly Gln Asn Lys Ala Gly Gln Val
                435                 440                 445

Trp His Asp Ile Thr Gly Asn Lys Pro Gly Thr Val Thr Ile Asn Ala
                450                 455                 460

Asp Gly Trp Ala Asn Phe Ser Val Asn Gly Gly Ser Val Ser Ile Trp
465                 470                 475                 480

Val Lys Arg

<210> SEQ ID NO 6
<211> LENGTH: 510
<212> TYPE: PRT
<213> ORGANISM: Artificial Sequence
<220> FEATURE:
<223> OTHER INFORMATION: Variant of enzyme from Bacillus licheniformis
<220> FEATURE:
<221> NAME/KEY: SIGNAL
<222> LOCATION: (1)..(29)
<220> FEATURE:
<221> NAME/KEY: mat_peptide
<222> LOCATION: (30)..(510)

<400> SEQUENCE: 6

Met Lys Gln Gln Lys Arg Leu Tyr Ala Arg Leu Leu Thr Leu Leu Phe
                -25                 -20                 -15

Ala Leu Ile Phe Leu Leu Pro His Ser Ala Ala Ala Ala Val Asn Gly
            -10                  -5                  -1   1

Thr Leu Met Gln Tyr Phe Glu Trp Tyr Thr Pro Asn Asp Gly Gln His
  5                  10                  15

Trp Lys Arg Leu Gln Asn Asp Ala Glu His Leu Ser Asp Ile Gly Ile
20                  25                  30                  35

Thr Ala Val Trp Ile Pro Pro Ala Tyr Lys Gly Thr Ser Gln Ala Asp
                40                  45                  50

Val Gly Tyr Gly Ala Tyr Asp Leu Tyr Asp Leu Gly Glu Phe His Gln
            55                  60                  65

Lys Gly Thr Val Arg Thr Lys Tyr Gly Thr Lys Gly Glu Leu Gln Ser
        70                  75                  80

Ala Ile Lys Ser Leu His Ser Arg Asp Ile Asn Val Tyr Gly Asp Val
    85                  90                  95

Val Ile Asn His Lys Gly Gly Ala Asp Ala Thr Glu Asp Val Thr Ala
100                 105                 110                 115

Val Glu Val Asp Pro Ala Asp Arg Asn Arg Val Ile Ser Gly Glu His
                120                 125                 130

Leu Ile Lys Ala Trp Thr His Phe His Phe Pro Gly Arg Gly Ser Thr
            135                 140                 145

Tyr Ser Asp Phe Lys Trp His Trp Tyr His Phe Asp Gly Thr Asp Trp
        150                 155                 160

Asp Glu Ser Arg Lys Leu Asn Arg Ile Tyr Lys Phe Gln Gly Lys Ala
    165                 170                 175
```

Trp Asp Trp Glu Val Ser Asn Glu Asn Gly Asn Tyr Asp Tyr Leu Thr
180                 185                 190                 195

Tyr Ala Asp Ile Asp Tyr Asp His Pro Asp Val Ala Ala Glu Ile Lys
            200                 205                 210

Arg Trp Gly Thr Trp Tyr Ala Asn Glu Leu Gln Leu Asp Gly Phe Arg
        215                 220                 225

Leu Asp Ala Val Lys His Ile Lys Phe Ser Phe Leu Arg Asp Trp Val
        230                 235                 240

Asn His Val Arg Glu Lys Thr Gly Lys Glu Met Phe Thr Val Ala Glu
245                 250                 255

Tyr Trp Gln Asn Asp Leu Gly Ala Leu Glu Asn Tyr Leu Asn Lys Thr
260                 265                 270                 275

Asn Phe Asn His Ser Val Phe Asp Val Pro Leu His Tyr Gln Phe His
                280                 285                 290

Ala Ala Ser Thr Gln Gly Gly Gly Tyr Asp Met Arg Lys Leu Leu Asn
            295                 300                 305

Gly Thr Val Val Ser Lys His Pro Leu Lys Ser Val Thr Phe Val Asp
        310                 315                 320

Asn His Asp Thr Gln Pro Gly Gln Ser Leu Glu Ser Thr Val Gln Thr
325                 330                 335

Trp Phe Lys Pro Leu Ala Tyr Ala Phe Ile Leu Thr Arg Glu Ser Gly
340                 345                 350                 355

Tyr Pro Gln Val Phe Tyr Gly Asp Met Tyr Gly Thr Lys Gly Asp Ser
                360                 365                 370

Gln Arg Glu Ile Pro Ala Leu Lys His Lys Ile Glu Pro Ile Leu Lys
            375                 380                 385

Ala Arg Lys Gln Tyr Ala Tyr Gly Ala Gln His Asp Tyr Phe Asp His
        390                 395                 400

His Asp Ile Val Gly Trp Thr Arg Glu Gly Asp Ser Ser Val Ala Asn
        405                 410                 415

Ser Gly Leu Ala Ala Leu Ile Thr Asp Gly Pro Gly Gly Ala Lys Arg
420                 425                 430                 435

Met Tyr Val Gly Arg Gln Asn Ala Gly Glu Thr Trp His Asp Ile Thr
                440                 445                 450

Gly Asn Arg Ser Glu Pro Val Val Ile Asn Ser Glu Gly Trp Gly Glu
            455                 460                 465

Phe His Val Asn Gly Gly Ser Val Ser Ile Tyr Val Gln Arg
        470                 475                 480

<210> SEQ ID NO 7
<211> LENGTH: 514
<212> TYPE: PRT
<213> ORGANISM: Bacillus amyloliquefaciens (SWISSPROT_P00692)
<220> FEATURE:
<221> NAME/KEY: SIGNAL
<222> LOCATION: (1)..(31)
<220> FEATURE:
<221> NAME/KEY: mat_peptide
<222> LOCATION: (32)..(514)

<400> SEQUENCE: 7

Met Ile Gln Lys Arg Lys Arg Thr Val Ser Phe Arg Leu Val Leu Met
    -30                 -25                 -20

Cys Thr Leu Leu Phe Val Ser Leu Pro Ile Thr Lys Thr Ser Ala Val
-15                 -10                 -5                  -1  1

Asn Gly Thr Leu Met Gln Tyr Phe Glu Trp Tyr Thr Pro Asn Asp Gly

```
              5                   10                  15
Gln His Trp Lys Arg Leu Gln Asn Asp Ala Glu His Leu Ser Asp Ile
             20                  25                  30
Gly Ile Thr Ala Val Trp Ile Pro Pro Ala Tyr Lys Gly Leu Ser Gln
 35                  40                  45
Ser Asp Asn Gly Tyr Gly Pro Tyr Asp Leu Tyr Asp Leu Gly Glu Phe
 50                  55                  60                  65
Gln Gln Lys Gly Thr Val Arg Thr Lys Tyr Gly Thr Lys Ser Glu Leu
             70                  75                  80
Gln Asp Ala Ile Gly Ser Leu His Ser Arg Asn Val Gln Val Tyr Gly
             85                  90                  95
Asp Val Val Leu Asn His Lys Ala Gly Ala Asp Ala Thr Glu Asp Val
            100                 105                 110
Thr Ala Val Glu Val Asn Pro Ala Asn Arg Asn Gln Glu Thr Ser Glu
            115                 120                 125
Glu Tyr Gln Ile Lys Ala Trp Thr Asp Phe Arg Phe Pro Gly Arg Gly
130                 135                 140                 145
Asn Thr Tyr Ser Asp Phe Lys Trp His Trp Tyr His Phe Asp Gly Ala
                150                 155                 160
Asp Trp Asp Glu Ser Arg Lys Ile Ser Arg Ile Phe Lys Phe Arg Gly
                165                 170                 175
Glu Gly Lys Ala Trp Asp Trp Glu Val Ser Ser Glu Asn Gly Asn Tyr
            180                 185                 190
Asp Tyr Leu Met Tyr Ala Asp Val Asp Tyr Asp His Pro Asp Val Val
            195                 200                 205
Ala Glu Thr Lys Lys Trp Gly Ile Trp Tyr Ala Asn Glu Leu Ser Leu
210                 215                 220                 225
Asp Gly Phe Arg Ile Asp Ala Ala Lys His Ile Lys Phe Ser Phe Leu
                230                 235                 240
Arg Asp Trp Val Gln Ala Val Arg Gln Ala Thr Gly Lys Glu Met Phe
                245                 250                 255
Thr Val Ala Glu Tyr Trp Gln Asn Asn Ala Gly Lys Leu Glu Asn Tyr
            260                 265                 270
Leu Asn Lys Thr Ser Phe Asn Gln Ser Val Phe Asp Val Pro Leu His
            275                 280                 285
Phe Asn Leu Gln Ala Ala Ser Ser Gln Gly Gly Gly Tyr Asp Met Arg
290                 295                 300                 305
Arg Leu Leu Asp Gly Thr Val Val Ser Arg His Pro Glu Lys Ala Val
                310                 315                 320
Thr Phe Val Glu Asn His Asp Thr Gln Pro Gly Gln Ser Leu Glu Ser
            325                 330                 335
Thr Val Gln Thr Trp Phe Lys Pro Leu Ala Tyr Ala Phe Ile Leu Thr
            340                 345                 350
Arg Glu Ser Gly Tyr Pro Gln Val Phe Tyr Gly Asp Met Tyr Gly Thr
            355                 360                 365
Lys Gly Thr Ser Pro Lys Glu Ile Pro Ser Leu Lys Asp Asn Ile Glu
370                 375                 380                 385
Pro Ile Leu Lys Ala Arg Lys Glu Tyr Ala Tyr Gly Pro Gln His Asp
                390                 395                 400
Tyr Ile Asp His Pro Asp Val Ile Gly Trp Thr Arg Glu Gly Asp Ser
                405                 410                 415
Ser Ala Ala Lys Ser Gly Leu Ala Ala Leu Ile Thr Asp Gly Pro Gly
            420                 425                 430
```

-continued

```
Gly Ser Lys Arg Met Tyr Ala Gly Leu Lys Asn Ala Gly Glu Thr Trp
        435                 440                 445

Tyr Asp Ile Thr Gly Asn Arg Ser Asp Thr Val Lys Ile Gly Ser Asp
450                 455                 460                 465

Gly Trp Gly Glu Phe His Val Asn Asp Gly Ser Val Ser Ile Tyr Val
                    470                 475                 480

Gln Lys

<210> SEQ ID NO 8
<211> LENGTH: 512
<212> TYPE: PRT
<213> ORGANISM: Bacillus licheniformis (SWISSPROT_P06278)
<220> FEATURE:
<221> NAME/KEY: SIGNAL
<222> LOCATION: (1)..(29)
<220> FEATURE:
<221> NAME/KEY: mat_peptide
<222> LOCATION: (30)..(512)

<400> SEQUENCE: 8

Met Lys Gln Gln Lys Arg Leu Tyr Ala Arg Leu Leu Thr Leu Leu Phe
                -25                 -20                 -15

Ala Leu Ile Phe Leu Leu Pro His Ser Ala Ala Ala Ala Ala Asn Leu
            -10                  -5                  -1   1

Asn Gly Thr Leu Met Gln Tyr Phe Glu Trp Tyr Met Pro Asn Asp Gly
          5                  10                  15

Gln His Trp Lys Arg Leu Gln Asn Asp Ser Ala Tyr Leu Ala Glu His
 20                  25                  30                  35

Gly Ile Thr Ala Val Trp Ile Pro Pro Ala Tyr Lys Gly Thr Ser Gln
                 40                  45                  50

Ala Asp Val Gly Tyr Gly Ala Tyr Asp Leu Tyr Asp Leu Gly Glu Phe
             55                  60                  65

His Gln Lys Gly Thr Val Arg Thr Lys Tyr Gly Thr Lys Gly Glu Leu
         70                  75                  80

Gln Ser Ala Ile Lys Ser Leu His Ser Arg Asp Ile Asn Val Tyr Gly
     85                  90                  95

Asp Val Val Ile Asn His Lys Gly Gly Ala Asp Ala Thr Glu Asp Val
100                 105                 110                 115

Thr Ala Val Glu Val Asp Pro Ala Asp Arg Asn Arg Val Ile Ser Gly
                120                 125                 130

Glu His Arg Ile Lys Ala Trp Thr His Phe His Phe Pro Gly Arg Gly
            135                 140                 145

Ser Thr Tyr Ser Asp Phe Lys Trp His Trp Tyr His Phe Asp Gly Thr
        150                 155                 160

Asp Trp Asp Glu Ser Arg Lys Leu Asn Arg Ile Tyr Lys Phe Gln Gly
    165                 170                 175

Lys Ala Trp Asp Trp Glu Val Ser Asn Glu Asn Gly Asn Tyr Asp Tyr
180                 185                 190                 195

Leu Met Tyr Ala Asp Ile Asp Tyr Asp His Pro Asp Val Ala Ala Glu
                200                 205                 210

Ile Lys Arg Trp Gly Thr Trp Tyr Ala Asn Glu Leu Gln Leu Asp Gly
            215                 220                 225

Phe Arg Leu Asp Ala Val Lys His Ile Lys Phe Ser Phe Leu Arg Asp
        230                 235                 240

Trp Val Asn His Val Arg Glu Lys Thr Gly Lys Glu Met Phe Thr Val
245                 250                 255
```

-continued

```
Ala Glu Tyr Trp Gln Asn Asp Leu Gly Ala Leu Glu Asn Tyr Leu Asn
260                 265                 270                 275

Lys Thr Asn Phe Asn His Ser Val Phe Asp Val Pro Leu His Tyr Gln
            280                 285                 290

Phe His Ala Ala Ser Thr Gln Gly Gly Gly Tyr Asp Met Arg Lys Leu
        295                 300                 305

Leu Asn Ser Thr Val Val Ser Lys His Pro Leu Lys Ala Val Thr Phe
    310                 315                 320

Val Asp Asn His Asp Thr Gln Pro Gly Gln Ser Leu Glu Ser Thr Val
325                 330                 335

Gln Thr Trp Phe Lys Pro Leu Ala Tyr Ala Phe Ile Leu Thr Arg Glu
340                 345                 350                 355

Ser Gly Tyr Pro Gln Val Phe Tyr Gly Asp Met Tyr Gly Thr Lys Gly
            360                 365                 370

Asp Ser Gln Arg Glu Ile Pro Ala Leu Lys His Lys Ile Glu Pro Ile
        375                 380                 385

Leu Lys Ala Arg Lys Gln Tyr Ala Tyr Gly Ala Gln His Asp Tyr Phe
    390                 395                 400

Asp His His Asp Ile Val Gly Trp Thr Arg Glu Gly Asp Ser Ser Val
405                 410                 415

Ala Asn Ser Gly Leu Ala Ala Leu Ile Thr Asp Gly Pro Gly Gly Ala
420                 425                 430                 435

Lys Arg Met Tyr Val Gly Arg Gln Asn Ala Gly Glu Thr Trp His Asp
            440                 445                 450

Ile Thr Gly Asn Arg Ser Glu Pro Val Val Ile Asn Ser Glu Gly Trp
        455                 460                 465

Gly Glu Phe His Val Asn Gly Gly Ser Val Ser Ile Tyr Val Gln Arg
    470                 475                 480

<210> SEQ ID NO 9
<211> LENGTH: 549
<212> TYPE: PRT
<213> ORGANISM: Bacillus stearothermophilus (SWISSPROT_P06279)
<220> FEATURE:
<221> NAME/KEY: SIGNAL
<222> LOCATION: (1)..(34)
<220> FEATURE:
<221> NAME/KEY: mat_peptide
<222> LOCATION: (35)..(549)

<400> SEQUENCE: 9

Met Leu Thr Phe His Arg Ile Ile Arg Lys Gly Trp Met Phe Leu Leu
                -30                 -25                 -20

Ala Phe Leu Leu Thr Ala Leu Leu Phe Cys Pro Thr Gly Gln Pro Ala
            -15                 -10                  -5

Lys Ala Ala Ala Pro Phe Asn Gly Thr Met Met Gln Tyr Phe Glu Trp
 -1  1               5                  10

Tyr Leu Pro Asp Asp Gly Thr Leu Trp Thr Lys Val Ala Asn Glu Ala
15                  20                  25                  30

Asn Asn Leu Ser Ser Leu Gly Ile Thr Ala Leu Trp Leu Pro Pro Ala
            35                  40                  45

Tyr Lys Gly Thr Ser Arg Ser Asp Val Gly Tyr Gly Val Tyr Asp Leu
        50                  55                  60

Tyr Asp Leu Gly Glu Phe Asn Gln Lys Gly Ala Val Arg Thr Lys Tyr
    65                  70                  75

Gly Thr Lys Ala Gln Tyr Leu Gln Ala Ile Gln Ala Ala His Ala Ala
```

```
                80                 85                  90
Gly Met Gln Val Tyr Ala Asp Val Val Phe Asp His Lys Gly Gly Ala
 95                 100                 105                 110

Asp Gly Thr Glu Trp Val Asp Ala Val Glu Val Asn Pro Ser Asp Arg
                115                 120                 125

Asn Gln Glu Ile Ser Gly Thr Tyr Gln Ile Gln Ala Trp Thr Lys Phe
                130                 135                 140

Asp Phe Pro Gly Arg Gly Asn Thr Tyr Ser Ser Phe Lys Trp Arg Trp
                145                 150                 155

Tyr His Phe Asp Gly Val Asp Trp Asp Glu Ser Arg Lys Leu Ser Arg
                160                 165                 170

Ile Tyr Lys Phe Arg Gly Ile Gly Lys Ala Trp Asp Trp Glu Val Asp
175                 180                 185                 190

Thr Glu Asn Gly Asn Tyr Asp Tyr Leu Met Tyr Ala Asp Leu Asp Met
                195                 200                 205

Asp His Pro Glu Val Val Thr Glu Leu Lys Ser Trp Gly Lys Trp Tyr
                210                 215                 220

Val Asn Thr Thr Asn Ile Asp Gly Phe Arg Leu Asp Ala Val Lys His
                225                 230                 235

Ile Lys Phe Ser Phe Phe Pro Asp Trp Leu Ser Asp Val Arg Ser Gln
240                 245                 250

Thr Gly Lys Pro Leu Phe Thr Val Gly Glu Tyr Trp Ser Tyr Asp Ile
255                 260                 265                 270

Asn Lys Leu His Asn Tyr Ile Met Lys Thr Asn Gly Thr Met Ser Leu
                275                 280                 285

Phe Asp Ala Pro Leu His Asn Lys Phe Tyr Thr Ala Ser Lys Ser Gly
                290                 295                 300

Gly Thr Phe Asp Met Arg Thr Leu Met Thr Asn Thr Leu Met Lys Asp
                305                 310                 315

Gln Pro Thr Leu Ala Val Thr Phe Val Asp Asn His Asp Thr Glu Pro
                320                 325                 330

Gly Gln Ala Leu Gln Ser Trp Val Asp Pro Trp Phe Lys Pro Leu Ala
335                 340                 345                 350

Tyr Ala Phe Ile Leu Thr Arg Gln Glu Gly Tyr Pro Cys Val Phe Tyr
                355                 360                 365

Gly Asp Tyr Tyr Gly Ile Pro Gln Tyr Asn Ile Pro Ser Leu Lys Ser
                370                 375                 380

Lys Ile Asp Pro Leu Leu Ile Ala Arg Arg Asp Tyr Ala Tyr Gly Thr
                385                 390                 395

Gln His Asp Tyr Leu Asp His Ser Asp Ile Ile Gly Trp Thr Arg Glu
                400                 405                 410

Gly Val Thr Glu Lys Pro Gly Ser Gly Leu Ala Ala Leu Ile Thr Asp
415                 420                 425                 430

Gly Pro Gly Gly Ser Lys Trp Met Tyr Val Gly Lys Gln His Ala Gly
                435                 440                 445

Lys Val Phe Tyr Asp Leu Thr Gly Asn Arg Ser Asp Thr Val Thr Ile
                450                 455                 460

Asn Ser Asp Gly Trp Gly Glu Phe Lys Val Asn Gly Gly Ser Val Ser
                465                 470                 475

Val Trp Val Pro Arg Lys Thr Thr Val Ser Thr Ile Ala Trp Ser Ile
                480                 485                 490

Thr Thr Arg Pro Trp Thr Asp Glu Phe Val Arg Trp Thr Glu Pro Arg
495                 500                 505                 510
```

```
Leu Val Ala Trp Pro
             515
```